(12) United States Patent
Tidor et al.

(10) Patent No.: US 6,230,102 B1
(45) Date of Patent: May 8, 2001

(54) COMPUTER SYSTEM AND PROCESS FOR IDENTIFYING A CHARGE DISTRIBUTION WHICH MINIMIZES ELECTROSTATIC CONTRIBUTION TO BINDING AT BINDING BETWEEN A LIGAND AND A MOLECULE IN A SOLVENT AND USES THEREOF

(75) Inventors: Bruce Tidor, Lexington; Lee-Peng Lee; Sara E. Dempster, both of Cambridge, all of MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 09/055,475

(22) Filed: Apr. 3, 1998

Related U.S. Application Data

(60) Provisional application No. 60/042,692, filed on Apr. 4, 1997.

(51) Int. Cl.[7] ............ G01N 33/48; G01N 33/50; G01N 33/00

(52) U.S. Cl. .............. 702/19; 702/20; 436/89; 364/496; 364/578

(58) Field of Search .................. 364/496, 578, 364/797, 499; 702/19, 20; 436/89

(56) References Cited

U.S. PATENT DOCUMENTS

| | | | |
|---|---|---|---|
| 4,939,666 | 7/1990 | Hardman | 364/496 |
| 5,081,584 | 1/1992 | Omichinski et al. | 364/497 |
| 5,579,250 | 11/1996 | Balaii et al. | 364/496 |
| 5,612,895 | 3/1997 | Balaii et al. | 364/496 |

OTHER PUBLICATIONS

Brooks et al : Proteins., advances in chem. physics, vol. LXXVI, pp. 136–174, John Wiley, 1988.*

Gao, J. et al., "Hidden Thermodynamics of Mutant Proteins: A Molecular Dynamics Analysis", *Science*, vol. 244, pp. 1069–1072, Jun. 2, 1989.

Klapper, I. et al., "Focusing of Electric Fields in the Active Site of Cu–Zu Superoxide Dismutase: Effects of Ionic Strength and Amino–Acid Modification", Proteins: Structure Function and Genetics, 1986, pp. 47–59.

Wong, C.F. et al., "Cytochrome c: A Molecular Proving Ground for Computer Simulations",*J. Phys. Chem.*, vol. 97. No. 13, 1993, pp. 3100–3110.

DesJarlais, R. L., Robert P. Sheridan, J. Scott Dixon, Irwin D. Kuntz and R. Venkatarghavan, "Docking Flexible Ligands to Macromolecular Receptors by Molecular Shape", *J. Med. Chem*, 289:2149–2153, 1986.

Connolly, Michael L., "Analytical Molecular Surface Calculation", *J. Appl. Cryst*, 16:548–558, 1983.

Richards, Frederic M., "Areas, Volumes, Packing, and Proteins Structure", *Ann. Rev. Biophys. Bioeng.*, 6:151–76, 1977.

Kuntz, Irwin D., Jeffrey M. Blaney, Staurt J. Oatley, Robert Langridge and Thomas E. Ferrin, "A geometric Approach to Macromolecule–Ligand Interactions", *J. Mol. Biol.*, 161:269–288, 1982.

Miranker, Andrew and Martin Karplus, "Functionality of Binding Sites: A Multiple Copy Simultaneous Search Method", *PROTEINS: Structure, Function, and Genetics.* 1:29–34, 1991.

Caflisch, Amedeo, Andrew Miranker And Martin Karplus, "Multiple Copy Simultaneous Search and Construction of Ligands in Binding Sites: Application to Inhibitors of HIV–1 Aspartic Proteinase", *J. Med. Chem.*, 36:2142–2167, 1993.

Eisen, Michael B., Don c. Wiley, Martin Karplus and Roderick E. Hubbard, "HOOK: A Program for Finding Novel Molecular Architectures That Satisfy the Chemical and Steric Requirements of a macromolecule Binding Site", *PROTEINS: Structure, Function, and Genetics.* 19:199–221, 1994.

Miranker, Andrew and Martin Karplus, "An Automated Method for Dynamic Ligand Design", *PROTEINS: Structure, Function, and Genetics.* 23:472–490, 1995.

Sitkoff, Doree, Kim A. Sharp and Barry Honig, "Accurate Calculation of Hydration Free Energies Using Macroscopic Solvent Models", *J. Phys. Chem.*, 98:1978–1988, 1994.

Yang, An–Suei and Barry Honig, "Free Energy Determinants of Secondary Structure Formation: I. α–Helices", *J. Mol. Biol*, 252:351–365, 1995.

(List continued on next page.)

*Primary Examiner*—John S. Brusca
*Assistant Examiner*—Stephen Siu
(74) *Attorney, Agent, or Firm*—Wolf, Greenfield & Sacks, P.C.

(57) ABSTRACT

The present computer-implemented process involves a methodology for determining properties of ligands which in turn can be used for designing ligands for binding with protein or other molecular targets, for example, HIV targets. The methodology defines the electrostatic complement for a given target site and geometry. The electrostatic complement may be used with steric complement for the target site to discover ligands through explicit construction and through the design or bias of combinatorial libraries. The definition of an electrostatic complement, i.e., the optimal tradeoff between unfavorable desolvation energy and favorable interactions in the complex, has been discovered to be useful in ligand design. This methodology essentially inverts the design problem by defining the properties of the optimal ligand based on physical principles. These properties provide a clear and precise standard to which trial ligands may be compared and can be used as a template in the modification of existing ligands and the de novo construction of new ligands. The electrostatic complement for a given target site is defined by a charge distribution which minimizes the electrostatic contribution to binding at the binding sites on the molecule in a given solvent. One way to represent the charge distribution in a computer system is as a set of multipoles. By identifying molecules having point charges that match this optimum charge distribution, the determined charge distribution may be used to identify ligands, to design drugs, and to design combinatorial libraries.

6 Claims, 5 Drawing Sheets

OTHER PUBLICATIONS

Yang, An Suei and Barry Honig, "Free Energy Determinants of Secondary Structure Formation: II. β–Sheets", *J. Mol. Biol*, 252:366–376, 1995.

Friedman, Richard A. and Barry Honig, "A Free Energy Analysis of Nucleic Acid Base Stacking in Aqueous Solution", *Biophysical Journal*, 69:1528–1535, 1995.

Zhou, Zhongxiang, Philip Payne and Max Vasquez, "Finite–Difference Solution of the Poisson–Boltzmann Equation Complete Elimination of Self–Energy", *Journal of Computational Chemistry*, 11(11):1344–1351, 1996.

Klapper, Issac, Ray Hagstrom, Richard Fine, Kim A. Sharp and Barry H. Honig, "Focusing of Electric Fields in the Active Site of Cu–Zu Superoxide Dismutase: Effects of Ionic Strength and Amino–Acid Modification", *PROTEINS: Structure, Function, and Genetics*. 1:47–59, 1986.

Gilson, Michael K., Kim A. Sharp and Barry H. Honig, "Calculating the Electrostatic Potential of Molecules in Solution: Method and Error Assessment", *Journal of Computational Chemistry*, 9(4):327–335, 1987.

Luty, Brock A., Malcolm E. Davis and J. Andrew McCammon, "Solving the Finite–Difference Non–Linear Poisson–Boltzmann Equation", *Journal of Computational Chemistry*, 13(9):1114–1118, 1992.

Zacharias, Martin, Brock A. Luty, Malcolm E. Davis and J. Andrew McCammon, "Poisson–Boltzmann Analysis of the $\lambda$ s Represor–operator Interaction", *Biophys J. Biophysical Society*, 63:1280–1258, Nov. 1992.

Zauhar, R. J. and R. S. Morgan, "The Rigorous Computation of the Molecular Electric Potential", *Journal of Computational Chemistry*, 9(2):171–187, 1988.

Bharadwaj, Ranganathan, Andreas Windemuth, S. Sridharan, Barry Honig and Anthony Nicholls, "The Fast Multipole Boundary Element Method for Molecular Electrostatics: An Optimal Approach for Large Systems", *Journal of Computational Chemistry*, 16(7):898–913, 1995.

\* cited by examiner a) XK 263
b) DMP 323
c) DMP 450

| COMPOUND | X, Y |
|---|---|
| A-77003 | R-OH, S-OH |
| A-76889 | R-OH, R-OH |
| A-76982 | S-OH, S-OH |
| A-78791 | S-OH, H |

```
                              SEQUENCE LISTING

<160> NUMBER OF SEQ ID NOS: 1

<210> SEQ ID NO 1
<211> LENGTH: 13
<212> TYPE: PRT
<213> ORGANISM: Influenza A virus

<400> SEQUENCE: 1

Pro Lys Tyr Val Lys Gln Asn Thr Leu Lys Leu Ala Thr
 1               5                  10
```

COMPUTER SYSTEM AND PROCESS FOR IDENTIFYING A CHARGE DISTRIBUTION WHICH MINIMIZES ELECTROSTATIC CONTRIBUTION TO BINDING AT BINDING BETWEEN A LIGAND AND A MOLECULE IN A SOLVENT AND USES THEREOF

RELATED APPLICATIONS

This application claims the benefit under 35 USC §119(e) of U.S. Provisional Patent Application Serial No. 60/042,692 filed on Apr. 4, 1997, entitled COMPUTER SYSTEM AND PROCESS FOR IDENTIFYING A CHARGE DISTRIBUTION WHICH MINIMIZES ELECTROSTATIC CONTRIBUTION TO BINDING AT BINDING BETWEEN A LIGAND AND A MOLECULE IN A SOLVENT AND USES THEREFOR. The contents of the provisional application are hereby expressly incorporated by reference.

GOVERNMENT SUPPORT

This work was funded in part by grant numbers GM 47678 and GM 56552 from the National Institutes of Health. Accordingly, the United States Government may have certain rights to this invention.

FIELD OF THE INVENTION

The present invention relates to rational drug design, and more particularly, to rational drug design based upon the prediction of a charge distribution on a ligand which minimizes the electrostatic contribution to binding between the ligand and its target molecule in a solvent. The present process also relates to methods and tools for making such predictions and enhanced-binding ligands, and to the diagnostic and therapeutic uses of the ligands so produced.

BACKGROUND OF THE INVENTION

Methods for computational rational drug design include two general approaches: those that screen whole molecules and those that probe local sites and construct molecules through the joining of molecular fragments or grafting of chemical moieties onto a parent structure. DOCK is an example of a whole-molecule algorithm which uses a procedure to find the complementary shape to a given target site (I. D. Kuntz, et al., J. Mol. Biol. 161:269 (1982) (Kuntz); R. L. DesJarlais, et al., J. Med. Chem. 31:722 (1988) (DesJarlais)). Large compound databases can be computationally "screened" by first eliminating molecules whose shape is incompatible with the target site (by computing an overlap with the complementary shape) and then by attempting to rank those that remain with an approximate energy function. This procedure has been successful at identifying a number of ligands that bind to target sites. Unfortunately, X-ray crystal studies have shown that the ligands often bind differently in the site than predicted. One possible reason for this discrepancy between prediction and reality is that although the shape-complementarity algorithm is effective at removing extremely incompatible trial ligands, the approximate energy function is too inexact to define higher-level details of binding.

The MCSS (Multiple Copy Simultaneous Search) algorithm is one of the most popular fragment based approaches to ligand design (P. J. Goodford, J. Med. Chem. 28:849 (1985); A. Miranker and M. Karplus, Proteins: Struct., Funct., Genet. 11:29 (1991); and A. Caflisch, et al., J. Med. Chem. 36:2142 (1993)). The essential idea is to search the region of a binding site and determine locations having especially favorable interaction energy with probes that represent a library of functional groups (carbonyl, amide, amine, carboxylate, hydroxyl, etc.). After the probes are successfully placed in the binding site, various subsets are linked to form coherent molecules. Two approaches to this problem have been developed. One attempts to fit small molecules from a database to join functional groups (HOOK) (M. B. Eisen, et al., Proteins: Struct., Funct., Genet. 19:199 (1995) and the other uses a simulated annealing protocol to grow linker atoms and bonds between fragments to produce ligand candidates with good covalent geometry and non-bonded interactions (DLD, dynamic ligand design) (A. Miranker and M. Karplus, Proteins: Struct., Funct., Genet. 11:29–34 (1991) and 23:472 (1995)).

The current methods for rational drug design are useful for suggesting novel and provocative geometries that appear to roughly compensate hydrogen-bonding groups in the site. Unfortunately, the current methods use approximations which may be inaccurate and which result in difficulties in accurately ranking candidates. Thus, although a number of computational algorithms exist both for the analysis of binding sites and bound complexes and for the rational design of ligands and other drug candidates, structure-based design remains an imprecise and non-deterministic endeavor.

SUMMARY OF THE INVENTION

The limitations of the prior art are overcome by providing for (i) a rigorous treatment of solvation, dielectric, and long-range electrostatic effects operating in both the unbound and the bound state of the target molecule and the ligand candidate, and (ii) a detailed quantitative method for ranking suggested ligands. The present process is based upon the discovery that the crude treatment of solvent, long-range electrostatics, and dielectric effects, as well as the lack of appropriate treatment for the unbound state of the target molecule and the ligand candidate, have limited the rational design and identification of novel ligand candidates for binding to a preselected target molecule. The present computer-implementation overcomes these limitations by providing a process which considers the exchange nature of ligand/target molecule binding, in which interactions with solvent are traded for interactions between a ligand and its complementary target molecule. In contrast to the prior art methods, the process disclosed herein takes into account solvent, long-range electrostatics, and dielectric effects in the binding between a ligand and its target receptor in a solvent.

Accordingly, in one aspect, a process for identifying properties of a ligand for binding to a target molecule (e.g., receptor, enzyme) in a solvent given a representation of a shape of the target molecule in three dimensions is provided. The process involves selecting a shape of the ligand defined in three dimensions, which shape is complementary to (matches) a shape of a selected portion of the target molecule; and determining a representation of a charge distribution on the ligand which minimizes the electrostatic contribution to binding between the ligand and the target molecule in the solvent. In some embodiments, the representation of the charge distribution is a set of multipoles. In other embodiments, the process further involves the step of identifying a molecule having point charges that match the representation of the charge distribution.

These methods are particularly useful for designing enhanced-binding ligands for binding to a target molecule which has a known ligand. As used herein, an enhanced-binding ligand refers to a ligand which has a structure that is based upon that of a known ligand for the target molecule but which is modified in accordance with the methods disclosed herein to have a charge distribution which minimizes the electrostatic contribution to binding between the ligand and the target molecule in a solvent. Thus, the present computer-implemented process provides a method of rational drug design that identifies such improved ligands for binding to a target molecule having a known or predictable three-dimensional structure. The method involves selecting a shape of the ligand defined in three dimensions which matches a shape of a selected portion of the target molecule and determining a representation of a charge distribution on the ligand which minimizes electrostatic contribution to binding between the ligand and the target molecule in the solvent.

The target molecules for which ligands are identified using the claimed process are molecules for which a representation of the three dimensional shape of the molecule is known or can be predicted. Such target molecules include biopolymers and non-biopolymers. Exemplary biopolymers include proteins, nucleic acids, lipids, carbohydrates, and mixtures of the foregoing (e.g., glycoproteins, lipoproteins and so forth). Exemplary non-biopolymers include polyamides, polycarbonates, polyalkylenes, polyalkylene glycols, polyalkylene oxides, polyalkylene terphthalates, polyvinyl alcohols, polyvinyl ethers, polyvinyl esters, polyvinyl halides, polyvinylpyrrolidone, polyglycolides, polysiloxanes, polyurethanes, alkyl cellulose, polymers of acrylic and methacrylic esters, polyethylene, polypropylene, poly(ethylene glycol), poly(ethylene oxide), poly(ethylene terphthalate), poly(vinyl alcohols), polyvinyl acetate, polyvinyl chloride, polystyrene, polyvinylpyrrolidone, polymers of lactic acid and glycolic acid, polyanhydrides, poly(ortho) esters, polyurethanes, poly(butic acid), poly(valeric acid), poly(lactide-cocaprolactone) and copolymers thereof.

As used herein, the terms "protein" or "polypeptide" are used interchangeably to embrace a variety of biopolymers that are formed of amino acids, e.g., receptors, hormones, and enzymes. It should be understood that as described herein, references to a "protein", a "polypeptide", or a "receptor" are generally applicable to analogous structures, such as lipoproteins, glycoproteins, proteins which have other organic or inorganic groups attached, and multi-chain and multi-domain polypeptide structures such as large enzymes and viruses, and include non-biopolymers. In these instances, analogous issues regarding the electrostatic contribution to binding between the ligand and the protein molecule are present.

In some embodiments, the target molecule is a protein and the present computer-implemented process is used to identify novel and/or improved ligands for binding to a protein having a known three-dimensional structure in a solvent. Known binding partners of ligands and proteins include hormone/receptor, cofactor or inhibitor/enzyme, antigen/antibody, and so forth. For proteins to which a ligand previously has been identified, the present process is used to identify the appropriate modifications to the known ligand structure to achieve a charge distribution on the "improved" ligand that minimizes the electrostatic contribution to binding between the improved ligand and the protein compared to that of the unmodified (natural) ligand. Exemplary ligand/protein binding partners used as starting points for identifying "improved" ligands in accordance with the present process are provided in the examples.

In another aspect, a process identifying novel and/or enhanced-binding ligands that bind to a target molecule that is a protein is provided. Proteins are known to fold into a three-dimensional structure which is dictated by the sequence of the amino acids (the primary structure of the protein) and by the solvent in which the protein is provided. The biological activity and stability of proteins are dependent upon the protein's three-dimensional structure. The three-dimensional structure of a protein can be determined or predicted in a number of ways. The best known way of determining a protein structure involves the use of X-ray crystallography. The three-dimensional structure of a protein also can be estimated using circular dichroism, light scattering, or by measuring the absorption and emission of radiant energy. Protein structure also may be determined through the use of techniques such as neutron diffraction, or by nuclear magnetic resonance (NMR). The foregoing methods are known to those of ordinary skill in the art and are described in standard chemistry textbooks (e.g., Physical Chemistry, 4th Ed. Moore, W. J., Prentiss-Hall N.J. (1972) and Physical Biochemistry, Van Holde, K. E., Prentiss-Hall, N.J. (1971)). Using the foregoing techniques, a number of recurring patterns in naturally occurring proteins have been identified, the most common of which are alpha helices, parallel beta sheets and anti-parallel beta sheets. See, e.g., R. Dickerson, et al., The Structure and Action of Proteins (1969). Together, the helices, sheets and turns of a protein's secondary structure produce the three dimensional structure of the active molecule. The three dimensional structure of proteins can be determined empirically using physical biochemical analysis or, alternatively, can be predicted using model building of three dimensional structures of one or more homologous proteins which have a known three dimensional structure.

The present computer-implemented process is particularly useful for designing an improved ligand that has a structure which is based upon the structure of a known ligand for a target molecule but which has been modified in accordance with the present methods to have a charge distribution which minimizes the electrostatic contribution to binding between the improved ligand and the target molecule in a solvent. Such improved ligands are referred to herein as "enhanced-binding ligands". Accordingly, the present process uses a ligand of known conformation as a starting point for the further optimization and selection of a ligand structure which will have reduced electrostatic contribution to binding to the molecule and the solvent. For example, the present process is used to produce an improved (enhanced-binding) co-factor or inhibitor of an enzyme (e.g., HIV-1 protease).

The present computer-implemented process also provides for the design of an improved hormone or other ligand for optimum binding (minimized electrostatic contribution to binding) to fit any known receptor site. This process is particularly useful for drug design, since it permits drugs to be designed and manufactured which more selectively and more stably are capable of binding to the receptor site. The design of improved ligands for binding to receptors means that lower dosages can be used, thereby reducing the chance of side effects and/or toxicity that may be associated with higher dosages. The design of improved ligands for binding to receptors also permits the identification of drugs having greater efficacy than the original ligand which is used as the basis for identifying an improved ligand having improved binding properties. Accordingly, known ligands for a protein can be used as a starting point for the design of improved ligands, wherein the improvement is based upon the improved binding properties of the ligand to the protein that are attributed to the selection of a ligand having a charge distribution which minimizes the electrostatic contribution to binding between the ligand and the protein in a solvent. Thus, the present process permits the customizing of antigens and epitopes to more selectively and, with greater affinity, bind to antibodies, and also provides for the design and selection of novel and/or improved ligands which bind to other receptors or target molecules.

The ligands that are identified in accordance with the methods disclosed herein can be labeled with detectable labels such as radioactive labels, enzymes, chromophores and so forth for carrying out immuno-diagnostic procedures or other diagnostic procedures. These labeled agents can be used to detect the target molecules in a variety of diagnostic samples. For imaging procedures, in vitro or in vivo, the ligands identified herein can be labeled with additional agents, such as NMR contrasting agents or x-ray contrasting agents. Methods for attaching a detectable agent to a polypeptide or other small molecule containing reactive amino groups are know in the art. The ligands also can be attached to insoluble support for facilitating diagnostic assays.

The present computer-implemented process also is useful for searching three-dimensional databases for structures which have a shape which matches a shape of a selected portion of the protein and which also has a charge distribution which minimizes electrostatic contribution to binding between the ligand and the protein in a solvent. Alternatively, three-dimensional databases can be selected on the basis of the shape of the ligand alone (so that it matches a shape of a selected portion of the protein) with further modification of the database molecules that satisfy this criteria to have a charge distribution which minimizes electrostatic contribution to binding between the modified ligand and the protein in a solvent. Search algorithms for three-dimensional database comparison are available in the literature. See, e.g., U.S. Pat. No. 5,612,895, issued to V. Balaji, et al., "Method of Rational Drug Design Based on Ab Initio Computer Simulation of Conformational Features of Peptides" and references disclosed therein. For related computer methods for drug design, see also, U.S. Pat. No. 5,081,584, issued to Omichinski et al., "Computer-assisted Design of Anti-peptides Based on the Amino acid Sequence of a Target Peptide", and U.S. Pat. No. 4,939,666, issued to Hardman, "Incremental Macromolecule Construction Methods".

Each of the novel and/or "improved" ligands identified using the present process are prepared employing standard synthetic or recombinant procedures and then tested for bioactivity. Those compounds which display bioactivity are candidate peptidomimetics; those compounds which do not display bioactivity help further define portions of the ligand which are essential for binding of the ligand to the target molecule. As used herein, a peptidomimetics broadly refers to a compound which mimics a peptide. For example, morphine is a peptidomimetic of the peptide endorphin.

A database of known compounds (e.g., the Cambridge Crystal Structure Data Base, Crystallographic Data Center, Lensfield Road, Cambridge, CB2 1EW, England; and Allen, F. H., et al., Acta Crystallogr., B35:2331 (1979)) also can be searched for structures which contain the steric (shape) parameters used for complementing (matching) a shape of a selected portion of the target molecule. Compounds which are found to contain the desired steric parameters are retrieved, and further analyzed to determine which of the retrieved compounds also have the desired charge distribution or that can be modified to have the desired charge distribution to minimize the electrostatic contribution to binding between the ligand and the target molecule in a solvent. Ligands that are found to contain both the desired shape and charge distribution are additional candidates as peptidomimetics of the original target peptides.

The ligands which are identified in accordance with the present computer-implemented process are evaluated for biological activity and/or for binding affinity to the target molecule. An iterative approach is used to identify the ligands having the most preferred biological properties. See, e.g., PCT WO 19359, "Process for making Xanthene or Cubane based compounds, and Protease Inhibitors", which describes an iterative process for identifying the bioactive conformation of an enzyme inhibitor in a complex chemical combinatorial library. The bioactive conformation then is used to design peptidomimetics, or used to search a three-dimensional database of organic structures to suggest potential peptidomimetics. Standard physiological, pharmacological and biochemical procedures are available for testing the "improved" or novel ligands identified using the present process. The particular protocol for evaluating bioactivity is a function of the compound that is being tested. This kind of analysis can be applied to known ligands that bind to a target molecule, (e.g., HIV protease, MHC class II proteins) to design enhanced-binding ligands for these biologically important target molecules.

DETAILED DESCRIPTION

The present computer-implemented process will be more completely understood through the following detailed description which should be read in conjunction with the attached drawing in which similar reference numbers indicate similar structures. All references cited above and in the following description are hereby expressly incorporated by reference.

The the present computer-implemented process involves a methodology for determining properties of ligands which in turn is used for designing ligands for binding with protein or other molecular targets, for example, HIV targets. The methodology defines the electrostatic complement for a given target site and geometry. The electrostatic complement may be used with a steric complement for the target site to discover ligands through explicit construction and through the design or bias of combinatorial libraries.

The definition of an electrostatic complement, i.e., the optimal tradeoff between unfavorable desolvation energy and favorable interactions in the complex, has been discovered to be useful in ligand design. This methodology essentially inverts the design problem by defining the properties of the optimal ligand based on physical principles. These properties provide a clear and precise standard to which trial ligands may be compared and used as a template in the modification of existing ligands and the de novo construction of new ligands.

The electrostatic complement for a given target site is defined by a charge distribution which minimizes the electrostatic contribution to binding at the binding sites on the molecule in a given solvent. One way to represent the charge distribution in a computer system is as a set of multipoles. By identifying molecules having point charges that match this optimum charge distribution, the determined charge distribution may be used to identify ligands, to design drugs, and to design combinatorial libraries.

Figure 1:
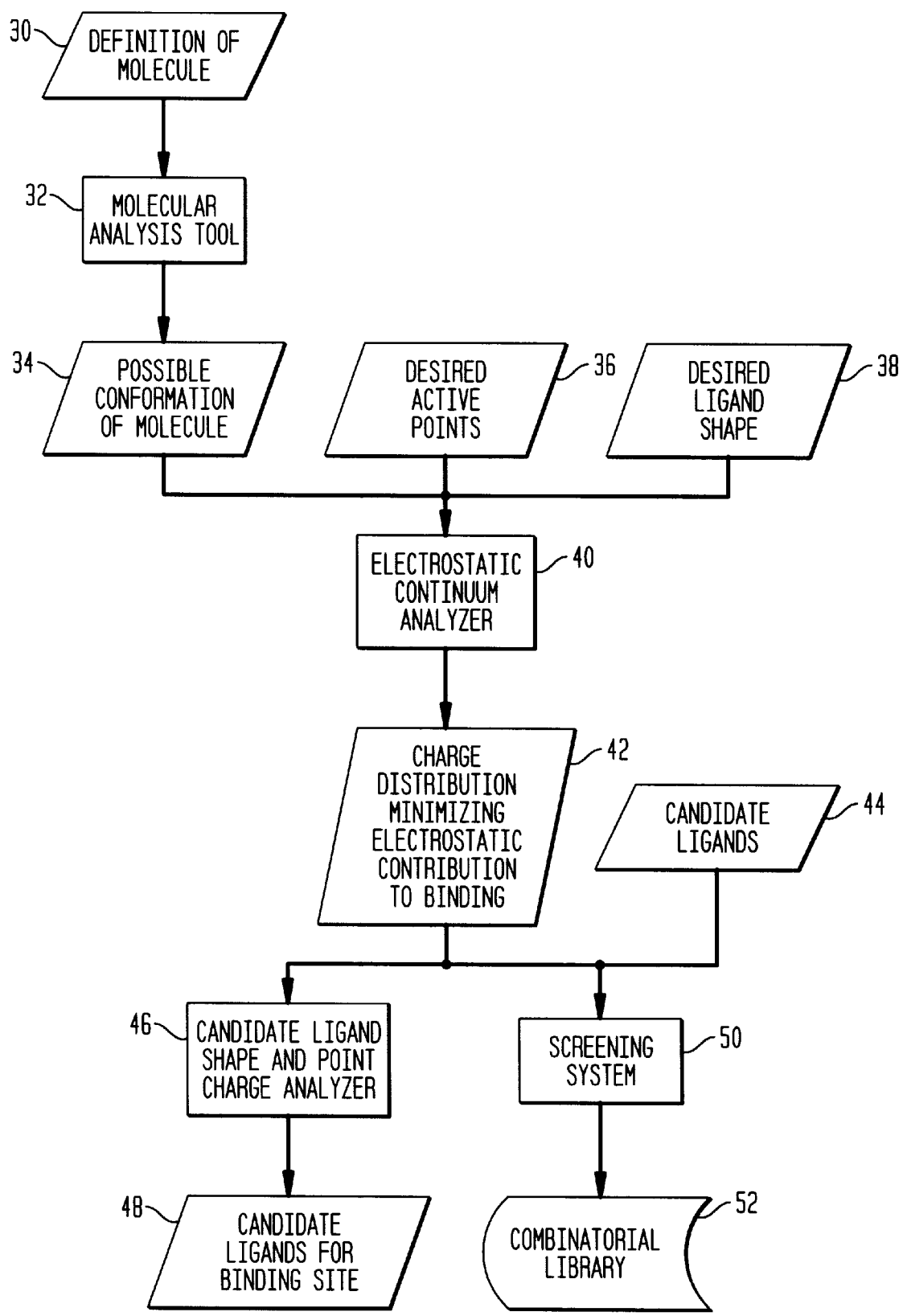
FIG. 1 is a block diagram describing one embodiment of the present computer-implemented process.

Referring now to FIG. 1, one embodiment of the present computer-implemented process is shown. This embodiment may be implemented using one or more computer programs on a computer system, an example of which is described below. Given a definition of a molecule for which a ligand is to be designed, indicated at 30, a molecular analysis tool 32 provides a possible conformation, or shape, of the molecule as indicated at 34. There are several systems available to provide such conformations, including but not limited to x-ray crystallography, homology modeling, nuclear magnetic resonance imaging or analytical techniques such as shown in Kuntz and DesJarlais. The desired binding or active points on the molecule, indicated at 36, and a desired ligand shape for binding with the molecule at the indicated binding points, as indicated at 38, also are input to the computer system.

An electrostatic continuum analyzer 40, described in more detail below, is used to determine a charge distribution which minimizes the electrostatic contribution to binding at the binding sites in a given solvent, given the representation of the shape of the molecule in three dimensions, the binding sites on the molecule defined by locations in three dimensions and the desired ligand shape, also defined in three dimensions. Accordingly, the output of analyzer 40 is a representation of a charge distribution minimizing electrostatic contribution to binding as indicated at 42.

The charge distribution 42 is used in combination with candidate ligands having the desired ligand shape, as indicated at 44. A candidate ligand shape and point charge analyzer 46 determines which candidate ligands have a charge distribution closest to the optimal charge distribution 42. Analyzer 46 outputs candidate ligands for the binding site as indicated at 48. Similarly, a screening system 50 may also be used to screen candidate ligands 44 for their proximity to the optimum charge distribution indicated at 42 in order to develop a combinatorial library 52. Such a combinatorial library may be used to develop more complex molecules having desired characteristics.

Figure 2:
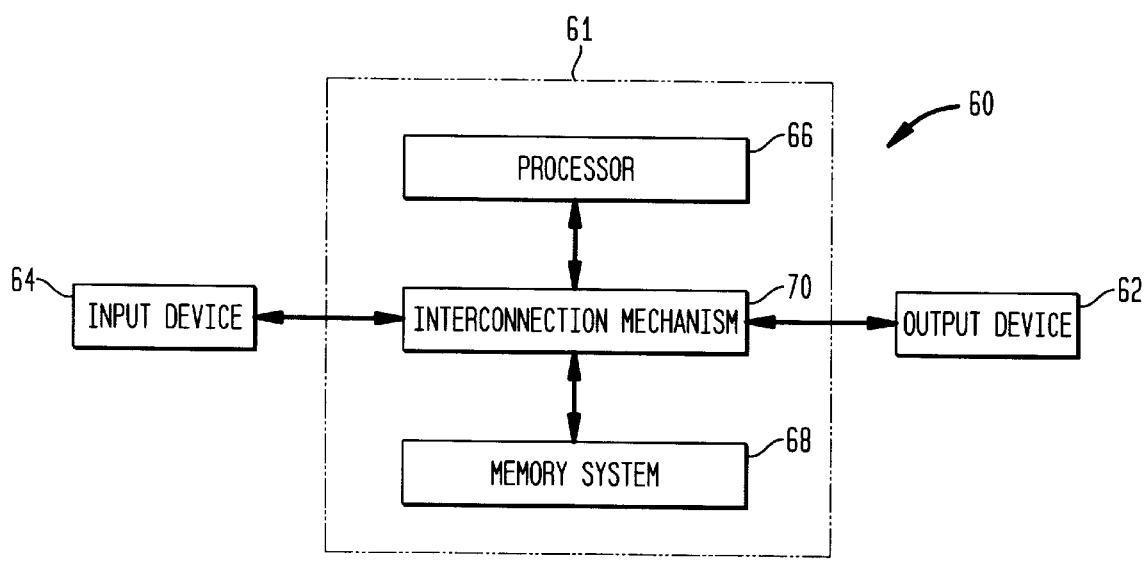
FIG. 2 is a block diagram of a computer system which may be used to implement the present computer-implemented process.

Referring now to FIG. 2, a suitable computer system 60 typically includes an output device 62 which displays information to a user. The computer system includes a main unit 61 connected to the output device 62 and an input device 64, such as a keyboard. The main unit 61 generally includes a processor 66 connected to a memory system 68 via an interconnection mechanism 70. The input device 64 is also connected to the processor 66 and memory system 68 via the connection mechanism 70, as is the output device 62.

It should be understood that one or more output devices may be connected to the computer system. Example output devices include a cathode ray tube (CRT) display, liquid crystal displays (LCD), printers, communication devices such as a modem, and audio output. It should also be understood that one or more input devices may be connected to the computer system. Example input devices include a keyboard, keypad, track ball, mouse, pen and tablet, communication device, audio input and scanner. It should be understood present computer-implemented process is not limited to the particular input or output devices used in combination with the computer system or to those described herein.

The computer system 60 may be a general purpose computer system which is programmable using a high level computer programming language, such as "C", "Fortran," or "Pascal." The computer system may also be specially programmed, special purpose hardware. In a general purpose computer system, the processor is typically a commercially available processor, of which the series x86 processors, available from Intel, and the 680X0 series microprocessors available from Motorola are examples. Many other processors are available. Such a microprocessor executes a program called an operating system, of which UNIX, DOS and VMS are examples, which controls the execution of other computer programs and provides scheduling, debugging, input/output control, accounting, compilation, storage assignment, data management and memory management, and communication control and related services. One embodiment was implemented using a Hewlett-Packard 9000/735 computer with a PA-7200 (99 MHz) chip. The processor and operating system define a computer platform for which application programs in high-level programming languages are written.

A memory system typically includes a computer readable and writeable nonvolatile recording medium, of which a magnetic disk, a flash memory and tape are examples. The disk may be removable, known as a floppy disk, or permanent, known as a hard drive. A disk has a number of tracks in which signals are stored, typically in binary form, i.e., a form interpreted as a sequence of one and zeros. Such signals may define an application program to be executed by the microprocessor, or information stored on the disk to be processed by the application program. Typically, in operation, the processor causes data to be read from the nonvolatile recording medium into an integrated circuit memory element, which is typically a volatile, random access memory such as a dynamic random access memory (DRAM) or static memory (SRAM). The integrated circuit memory element allows for faster access to the information by the processor than does the disk. The processor generally manipulates the data within the integrated circuit memory and then copies the data to the disk when processing is completed. A variety of mechanisms are known for managing data movement between the disk and the integrated circuit memory element, and the present process is not limited thereto. It should also be understood that the present process is also not limited to a particular memory system.

It should be understood the present computer-implemented process is not limited to a particular computer platform, particular processor, or particular high-level programming language. Additionally, the computer system 60 may be a multiprocessor computer system or may include multiple computers connected over a computer network.

Defining Ligand Properties

Figure 3:
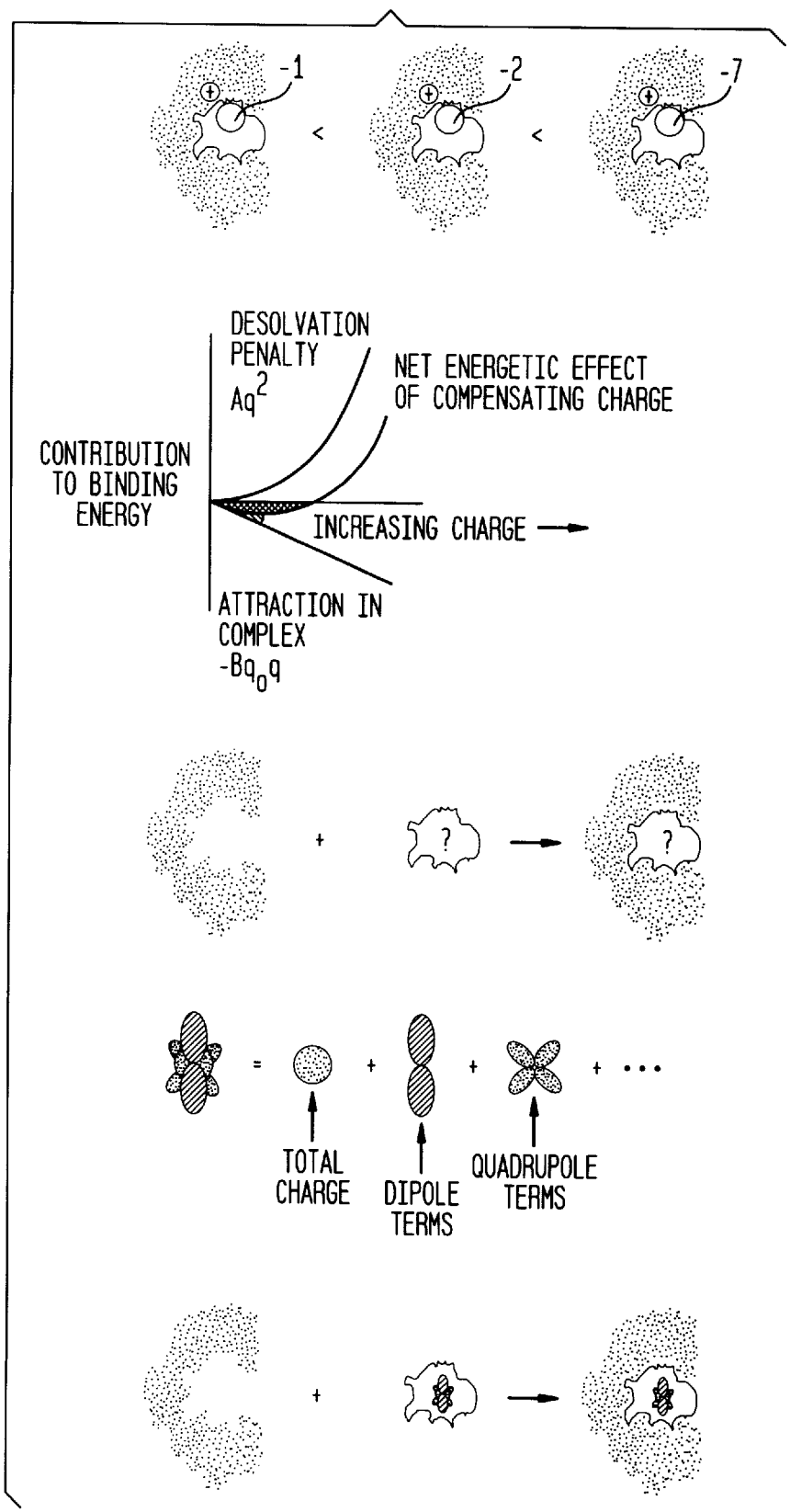
FIG. 3 is a diagram illustrating chemical principles underlying the present computer-implemented process.
Figure 4A:
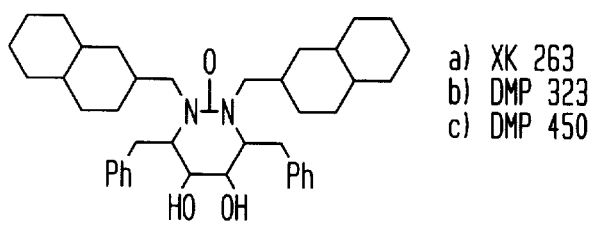
FIG. 4 is a diagram illustrating inhibitors of HIV-1 protease.
Figure 4B:
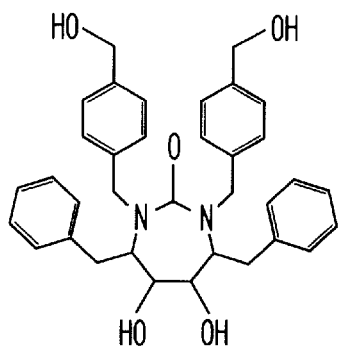
Figure 4C:
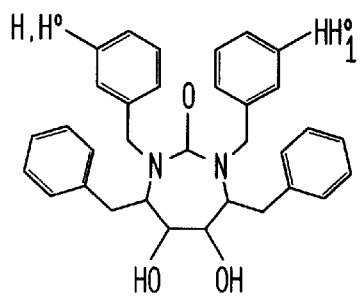
Figure 4D:
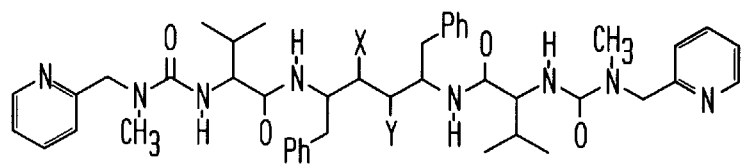

The process for defining complementary ligand properties of electrostatic interactions, using such continuum calculations is outlined in FIG. 3. Because of the exchange nature of electrostatic interactions, seemingly "strong" electrostatic attractions found in the bound state frequently destabilize the binding equilibrium, but presumably contribute to specificity. That is, because of the substantial desolvation penalty incurred for burying polar and charged groups, their net electrostatic contribution to macromolecular association is generally unfavorable. In designing a ligand for a given, fixed target that has polar and charged groups at the site, it is important to balance the desolvation and interaction energies so as to contribute most favorably to binding or at least to provide the smallest possible destabilization. The following method solves this problem analytically, using idealized geometries and a continuum electrostatic model, and provides a single, unique optimum which is solved exactly.

For the case of binding a spherical ligand to an arbitrarily shaped receptor to form a spherical complex, the free energy of binding is expressed in terms of the charge multipoles of the ligand. By minimizing the binding free energy with respect to the multipoles, (i) there is a single, optimal multipole distribution defining the tightest binding ligand for the given geometry, (ii) this multipole distribution corresponds to a minimum in $\Delta G_{binding}$, (iii) at this optimum the magnitude of the ligand desolvation penalty is exactly half the magnitude of the favorable intermolecular electrostatic interactions in the complex, and (iv) the loss in binding free energy for a sub-optimal charge distribution is easily calculated by comparing to the optimum. This minimization of the binding free energy with respect to the multipoles provides a clear and unambiguous route from the continuum model, an accepted energetic description of macromolecules and ligands to a set of descriptors, i.e., the multipoles, for the optimal ligand. For this method to be broadly applicable, any requirement for spherical geometries is removed. Accordingly, macromolecules and ligands are of arbitrary shape and are treated as such.

In the spherical case, a variational binding energy for optimization, is defined as follows:

$$\Delta G_{var} = \Delta G_{int,L-R} + G_{hyd,L}^{bound} - G_{hyd,L}^{unbound} \quad (1)$$

This includes three terms, which are discussed separately here. The first is the ligand-receptor screened interaction energy, which includes a contribution from the interaction of each multipole component of the ligand charge distribution with all point charges in the receptor. These contributions are accounted for by coefficients, the $\alpha_{l,m}$, which are computed analytically, and the ligand multipoles ($Q'_{l,m}$), $$\Delta G_{int,L-R} = \sum_{l=0}^{\infty} \sum_{m=-l}^{l} \alpha_{l,m} Q'^*_{l,m} \quad (2)$$

The second term is the bound-state reaction-field energy due to the ligand charge distribution, $G_{hyd,L}^{bound}$. It has contributions from all pairs of multipole components with the same value of m, since the ligand multipole distribution is generally expanded about a point that is not the center of the spherical boundary in the bound state but the geometry is chosen with azimuthal symmetry, $$G_{hyd,L}^{bound} = \sum_{l=0}^{\infty} \sum_{m=-l}^{l} \sum_{l'=0}^{\infty} \beta_{l,m,l',m} Q'^*_{l,m} Q'_{l',m} \quad (3)$$

The third term is the unbound-state solvation energy, which involves a contribution from each multipole component. Because the multipole expansion is taken about the center of the ligand sphere, and due to the orthogonality of the spherical harmonics, all cross-terms cancel, giving $$G_{hyd,L}^{unbound} = \sum_{l=0}^{\infty} \sum_{m=-l}^{l} \gamma_{l,m} Q'^*_{l,m} Q'_{l,m} \quad (4)$$

Combining the above three equations, $$\Delta G_{var} = \sum_{l=0}^{\infty} \sum_{m=-l}^{l} \alpha_{l,m} Q'^*_{l,m} + \sum_{l=0}^{\infty} \sum_{m=-l}^{l} \sum_{l'=0}^{\infty} (\beta_{l,m,l',m} - \delta_{l,l'} \gamma_{l,m}) Q'^*_{l,m} Q'_{l',m} \quad (5)$$

and transforming to matrix notation, one completes the square and solves for the $Q'^{opt}_{l,m}$ giving the optimal variation binding energy. Since terms neglected from the variational binding energy are constant for a given geometry, these describe the multipoles of the optimal binding ligand. A more detailed exposition of this process is set forth in the article by L. P. Lee and B. Tidor, J. Chem. Phys., 106:8681–8690, (1997), which is expressly incorporated herein by reference and part of which can also be found in the Appendix.

An implementation of a computer program to perform the kinds of processing outlined in Lee and Tidor, supra and in the Appendix, can receive as an input the value $l_{max}$, which determines the size of the matrix of equations 59 and 61 (see Appendix), $l_{cut}$, which truncates the innermost summation in equations 25 and 46 (see Appendix), the geometry of the problem, which indicates the shape of the target and the ligand, and whether the monopole of the optimum is to be free or fixed at some value. The geometry of the problem includes the radius and coordinates of the center of both the bound state and ligand spheres on the z axis and the coordinates of magnitude of each partial atomic charge in the system. The dielectric constants $\in_1$ and $\in_2$ are determined by the particular problem. Evaluation of the $\alpha_i$, $\beta_{ij}$ and $\gamma_i$ values is carried out, followed by solution of matrix equation 59 or 61 (see Appendix), for example by using LU decomposition. The eigen values of the B matrix may be obtained to verify that the stationary point was a minimum. All real floating point values may be represented, for example, using 64 bits or other suitable format. The computation of the matrix algebra may be accomplished using available or increased precision versions of appropriate subroutines, such as defined in Press et al, *Numerical Recipes in C: The Art of Scientific Computing*, Cambridge University Press, Cambridge, 1988. The output of the program when executed is a representation of the optimal charge distribution (e.g., using multipoles), the nature of the stationary point and a file recording the alpha, beta and gamma values. Because a direct method, i.e., LU decomposition, was used to solve a matrix equation, the time scales as $(l_{max})^6$ and the memory used scales as $(l_{max})^4$. This program output may be improved by accounting for the particularly sparse matrix in the matrix equation. Optimizations also may be provided by solving the matrix equation with iterative methods such as the conjugate gradient method or various relaxation methods. This method has been implemented and tested using both a highly symmetric charge distribution and the terminus of an alpha-helix as the receptor.

This method is extended to arbitrarily shaped molecules, by using iterative numerical computation to calculate the corresponding matrix coefficients and, for efficiency, by using a number of centers dispersed through the ligand volume at which individual multipole expansions are located.

When this method is extended to non-spherical geometries, it takes the following form. The $\alpha_{l,m}$ retain the same character, the $\beta_{l,m,l',m}$ become $\beta_{l,ml',m'}$ because azimuthal alignment can no longer be used and the $\gamma_{l,m}$ become $\gamma_{l,m,l',m'}$ because the orthogonality of the spherical harmonics does not eliminate the cross-terms for a non-spherical surface. Thus, a very similar matrix equation is found, $$\Delta G_{\text{var}} = \sum_{l=0}^{\infty}\sum_{m=-l}^{l} \alpha_{l,m} Q'^{*}_{l,m} + \sum_{l=0}^{\infty}\sum_{m=-l}^{l}\sum_{l'=0}^{\infty}\sum_{m'=-l'}^{l'} (\beta_{l,m,l',m'} - \gamma_{l,m,l',m'}) Q'^{*}_{l,m} Q'^{*}_{l',m'} \qquad (6)$$

which is solvable by the same matrix methods used for the spherical case or by singular value decomposition using available or improved precision versions of appropriate subroutines, such as defined in Press et al, supra. However, numerical computations may be used to calculate the corresponding matrix coefficients. For the spherical case above, closed form expressions may be derived for rapid computation. When the same matrix coefficients ($\alpha_{l,m}$, $\beta_{l,m,l',m'}$ and $\gamma_{l,m}$) are computed using iterative numerical methods, the computing requirements increase substantially.

Alternatively, the ligand may be described by using more centers, each described by a small number of multipoles. In the extreme, each ligand can be composed on point-charge locations, and currently 500 would be affordable, i.e., computable in under three weeks of computer time, with $l_{max}=0$ at each center. It is likely that the best solution will be intermediate, in which there are roughly 10 locations with $l_{max}=2$ (monopole, dipolar, and quadrupolar terms) or so at each center. The distributed centers of low-order multipoles may be an efficient and accurate way to describe arbitrary ligand charge distributions. The method has been properly elaborated for inclusion of interactions between separate multipole centers, and results using spherical geometries indicate that using two multipole distributions rather than one allows an equivalent description of the optimal charge distribution to be achieved using roughly one-quarter the number of multipole components and thus essentially one-quarter the time.

Two alternative schemes may be used for iterative numerical computation of matrix coefficients. The first scheme is a modification of a finite-difference Poisson-Boltzmann (FDPB) solver, such as DELPHI (I. Klapper, R. Hagstrom, R. Fine, K. Sharp. and B. Honig). Focusing of electric fields in the active site of Cu—Zn superoxide dismutase: Effects of ionic strength and amino-acid modification. Proteins: Struct., Funct., Genet. 1: 47–59 (1986), M. K. Gilson, K. A. Sharp, and B. H. Honig. Calculating the electrostatic potential of molecules in solution: Method and error assessment. J. Comput. Chem. 9: 327–335 (1988) and UHBD (B. A.

Luty, M. E. Davis, and J. A. McCammon. Solving the finite-difference non-linear Poisson-Boltzmann equation. J. Comput. Chem. 13: 1114–1118 (1992), M. Zacharias, B. A. Luty, M. E. Davis, and J. A. Mcammon. Poisson-Boltzmann analysis of the λ repressor-operating interaction. Biophys. J. 63: 1280–1285 (1992)), and the second scheme is a modification of boundary-element methods (BEM) (R. J. Zauhar and R. S. Morgan. The rigorous computation of the molecular electric potential. J. Comput. Chem. 9: 171–187 (1988), R. Bharadwaj, A. Windemuth, S. Sridharan, B. Honig, and A. Nicholls. The fast multipole boundary element method for molecular electrostatics: An optimal approach for large systems. J. Comput. Chem. 16: 898–913 (1995)). These modifications allow point multipoles, as opposed to just point charges, to be represented.

Thus, a more complex method includes the following. For each pole component at each center iterative continuum calculations are carried out to determine its screened coulombic interaction with the receptor point charges (essentially $\alpha_{l,m}$), its interaction with its own reaction field and that of each of the other pole components in the system in the bound (essentially $\beta_{l,m,l',m'}$) and unbound (essentially $\gamma_{l,m,l',m'}$) state. It is estimated that a ligand represented by 99 pole components (such as 11 centers with $l_{max}=2$ at each) will require under three weeks of CPU time. For many applications, half that number of centers and half the time could be sufficient. A multipole distribution about a single center uses many global terms to accurately describe a complex charge distribution fairly far from the center. By distributing in space a number of centers for the expansion, an equally accurate description can be obtained with many fewer, somewhat more local, terms.

Using Molecular Descriptors to Discover Ligands

Referring again to FIG. 1, the charge distribution 42 defined by the above procedure may be used to determine which candidate ligands would have a charge distribution closest to the optimum. The descriptions of the charge distribution and molecular shape can be used to construct ligand structures de novo, or they can be used to screen compound databases, or they can be used in the design or bias of combinatorial libraries.

In the process of discovering ligands, detailed point-charge distributions are fit to the multipole distributions determined using the above methods. Next, molecular fragments and/or molecules are fit to the point-charge distributions. Finally, both the point charges and the fragments may be used in the design of combinatorial libraries, described below.

A least squares fitting procedures may be used to define a point-charge distribution that is a close fit to the multipole distribution describing the optimum. For example, a regular cubic lattice of grid points with roughly the spacing used in FDPB computations may be used. This can be achieved using the same tri-linear function used in FDPB codes to carry out the mapping in the opposite direction arbitrary point charges mapped to charged lattice points. (See Klapper.) Whether a set of point charges can provide an adequate fit to the electrostatic charge distribution represented by the multipoles, can be determined by comparing the decrease in free energy of binding due to using the fit point-charge distribution in place of the multipoles themselves. A trial using a cubic lattice of grid points with 0.5-Å spacing indicates that the computed loss in binding energy is less than 0.001 kcal/mol due to fitting point charges. In addition, the resulting point charges assigned are reasonable in magnitude (nearly all are less than 0.10e), making a fit to molecular fragments plausible. In this embodiment the multipoles, which are a somewhat non-local description of the charge distribution, are converted into a local grid based point-charge description so molecules can be fit.

The effectiveness of set points in fitting charges may be measured not only by minimizing the loss in binding energy, but also by how simply molecules or molecular fragments may be constructed from the point charges. The cubic lattice is used as described above to fit functional groups and molecules. A more molecule-based grid may also be used and may include connectivity for the common valencies (sp $sp^2$, and $sp^3$) co-embedded. Additionally, a uniform density of point charges may be a disadvantage, rather, having a higher density of point charges near the ligand surface may provide a more effective fit.

Given a point-charge distribution, it may be fit to a molecule or molecular fragment in several ways. For example, a database of molecular fragment geometries and point-charge distributions (such as a library derived from the PARSE parameter set of fragments (D. Sitkoff, K. Sharp, and B. Honig. Accurate calculation of hydration free energies using macroscopic solvent models. J. Phys. Chem. 98: 1978–1988 (1994)), may be used to match individual functional groups to favorable locations on the point-charge distribution. This matching process could be a very large scanning search if each fragment needed to be attempted at all locations and in every orientation in the ligand volume. The timing may be improved substantially, though, using a regular cubic lattice for the point-charge distribution. Each fragment would only need to be scanned over a relatively small section of lattice to determine sets of lattice point charges "diagnostic" for it. These diagnoses may be compiled for all library fragments, for example, in a hash table, and clusters of point-charge values may be used to query the hash table and fit fragments to the charge lattice. So long as the same grid spacing is maintained, the hash table may be reused for many different targets and optimizations.

After fragments have been placed, the problem of fitting them together into molecules is similar to the one addressed by the MCSS algorithm described above, although the theoretical foundations for choosing fragment locations are very different in that method and in the present computer-implemented process. Two solutions developed there may be adapted for use here. In the HOOK method described above, a database of small molecules is used as linkers to fit fragments together, generally trying to introduce rigidity at the same time. In the dynamic ligand method (DLD) described above, a sea of carbon atoms is superposed with the fragments and a simulated annealing procedure is used in which the occupancy of each carbon can grow and shrink and in which bond-making and bond-breaking events are used to coalesce novel carbon linkers. In each method, each fragment generally is allowed to move somewhat in order to create relatively unstrained ligands. An accurate penalty function for movement based on how movement affects the computed binding energy may be used. The DLD based approach may be better because of its flexibility.

Alternatively, molecules may be grown in a sequential fashion so as to fill the ligand volume and fit the point-charge distribution. A straightforward scheme involves placing a single fragment at a location where it fits the point-charge field and executing a search for other fragments that can be joined to the first, adjusting their relative orientation via the connecting torsion. This procedure can be carried out in a tree-like manner to create large numbers of ligands. An appropriate figure of merit or distance metric, is applied to determine whether to accept or reject each new fragment. A potential that includes van der Waals and torsional terms as well as a fit to the volume and charge distribution of the defined optimum may be used in this method.

Yet another alternative is the design of "minimalist" ligands. The multipole distributions of the optima may be fit with as few point charges as possible. This optimization process involves finding a relatively small number of point charges whose computed binding energy is within a few tenths of a kcal/mol of the optimum. Studies with complementary nucleotide bases suggest that a better complementary "base" than that used by nature can be reconstructed using only one-third the number of pont charges, i.e., a complement to adenine can be constructed using only four point charges, and this complement binds tighter than adenine. These reduced point-charge ligands retain the Watson-Crick hydrogen bonding to the partner, although in somewhat different fashion. Models for ligands containing very few required point charges may represent the key compensating interactions that a more elaborate ligand should contain. They may serve as useful scaffolds or seeds upon which further computational molecular design should be carried out or about which a synthetic combinatorial strategy could usefully be built. If they bind tightly enough, they may be particularly useful therapeutics because it may be very difficult for the virus to evolve resistance to a small ligand targeted to catalytic side chains.

Designing Combinatorial Libraries

The design of combinatorial libraries as illustrated at 50 in FIG. 1, will now be described in more detail. Although there is substantial long-standing interest in using computational molecular modeling to carry out de novo rational ligand design, there are other ways in which this method can be used for ligand discovery. In particular, this method can be used to define a relatively narrow region of chemical space, and a combinatorial library can be designed to search that limited space particularly thoroughly. Given the finite synthetic capacity of even the most ambitious combinatorial chemistry schemes, this mechanism can channel synthetic diversity into higher probability directions.

Again, there are several alternative implementations for this computational method. One implementation begins with detailed grids of point charges fit to the optimal multipoles and segregates the grid into regions of space corresponding to pockets appropriate for receiving one or more functional groups. The shape and point charges are then used to assign the general size and character, e.g., positively charged, negatively charged, highly polar, moderately polar, weakly polar, or hydrophobic. These property definitions may be used to bias combinatorial synthesis towards generating appropriate ligands.

Having described the computational aspects of the present computer-implemented process some biological model systems will now be described.

Biological Model Systems

EXAMPLE 1

Class II Major Histocompatibility Complex (MHC) Proteins

Introduction

The major histocompatibility complex proteins (MHC) are cell-surface antigen presenting structures whose role is to display a sample of proteolized intracellular peptide to T cells. Recognition of a peptide as "foreign" by a T cell induces an immune response. This response includes killing the antigen-presenting cell (class MHC, usually) or secreting lymphokines that control attack by various elements of the immune system, including B cell activation (class II MHC, usually). Because each individual has a limited number of histocompatibility proteins and a virtually unlimited number of peptides to present, each MHC molecule is capable of presenting a wide variety of peptides. Structural studies have revealed separate mechanisms used by class I and class II MHC molecules for achieving high affinity yet fairly low specificity (L. J. Stem and D. C. Wiley, Structure 2:245 (1994)).

The structure of the HLA-DR1 class II MHC protein complexed with a peptide from influenza virus has been solved (L. J. Stern, et al., Nature (London) 368:215 (1994)). The original structure of HLA-DR1 in complex with influenza hemagglutinin residues 306–318 (PKYVKQNTLKLAT) elucidated a number of important features of binding and recognition that have been confirmed in other class II MHC complexes. The protein is comprised of an eight-stranded beta-sheet with two immunoglobulin-like domains on the cell-surface side and a pair of alpha-helices on the extracellular side. The peptide-binding site is a cleft between the two helices and supported by the beta-sheet. The peptide binds in an extended but highly twisted conformation, similar to the type II polyproline helical conformation; the N- and C-termini extend outside of the site. Most of the hydrogen bonds between peptide and protein (12 of 15) are to peptide backbone groups, which helps to explain how the protein recognizes many different peptides. The observed peptide conformation forces each peptide side chain into one of three directions: 5 of the side chains (Y308, Q311, T313, L314, and L316) are directed into pockets in the surface of the MHC molecule and are essentially buried, 6 of the side chains (K307, V309, K310, N312, K315, and T318) are directed out away from the binding site and toward the T cell receptor, and the remaining 2 side chains (P306 and A317) are directed across the site. Thus, residues making extensive contact with the MHC are, for the most part, distinct from those poised to interact with approaching T cell receptors. Of the 5 pockets, the deepest accommodates Tyr308, though binding studies shown that tyrosine, phenylalanine, or tryptophan are all allowed. Different class II MHC alleles incorporate substitutions at the 5 pockets that receive the 5 buried side chains. It is thought that alterations in these interactions are responsible for allotypic differences in peptide specificity. Because individuals differ in their allotypic complement of MHC molecules, individuals differ in the profile of their immune response.

The relative affinity of peptides for binding to individual class II MHC molecules is thought to be responsible for relative peptide antigenicity. Phage display selection and amplification studies have defined the frequency with which each amino acid is found at individual positions in high-affinity peptides (J. Hammer, et al., J. Exp. Med. 176:1007 (1992) and J. Hammer, et al., PNAS U.S.A. 91: 4456 (1994)). The strongest anchor position was determined to be a large aromatic at position 1, which was found as Tyr (48%), Phe (25%), or Trp (13%) predominantly. Position 4 was a long hydrophobe, found as Met (50%) and Leu (28%); position 6 was a small residue, found as Ala (32%) and Gly (22%); and position 9 was generally found as Leu (45%).(J. Hammer, et al., J. Exp. Med. 176:1007 (1992)). Also, there were very few negatively charged side chains recovered at any position. This data provides a useful semi-quantitative set of relative affinities that are useful for validating the computational methodology of the present process.

Testing and Validation

The class II MHC HLA-DR1 system is used to test the computational methodology disclosed herein to analyze the peptide-binding site, and to design enhanced-binding molecules. Testing and validation consists of a number of tasks, initially using the crystal structure with bound viral peptide (L. J. Stem, et al., Nature (London) 368:215 (1994)). These tests are designed to confirm that the methods are capable of (i) recognizing that the observed bound peptide is a good binder, (ii) recognizing that known deleterious peptide mutations are unfavorable, (iii) recognizing that known enhanced-binding peptide mutations are favorable, (iv) reproducing the known pattern of binding hydrophobic, polar, and charged residues in individual surface pockets, and (v) regenerating the known peptide backbone conformation and contacts.

Analysis of Bound-Peptide Complex

The binding of viral peptide to HLA-DR1 is analyzed using the methods disclosed herein. Briefly, the strategies disclosed herein are used to regenerate the bound peptide's charge distribution. A variable point charge is placed on each atom of the peptide and the charge values are computed that optimize the free energy of binding. By comparing these point charges to the actual point charges, the reduction in affinity of the peptide compared to the calculated optimum can be computed. Discrepancies from point charges between the calculation and the actual point charges of the viral peptide suggest that the possibility exists to design an enhanced-binding ligand. In this manner, this set of tests is used to confirm the asserted utility of the claimed methods with respect to designing an enhanced-binding ligand based upon the structure of a known ligand and its binding partner.

Enhanced- and Reduced-Binding Mutations

Tests of relative affinity are performed initially using isosteric or near-isosteric replacements. From the data of Hammer et al. using phage display studies, Tyr is preferred over Phe at position 1, and Met or Leu is preferred over Gln at position 4, where the underlined residue corresponds that in the bound peptide structure (L. J. Stem, et al., Nature (London) 368:215 (1994); J. Hammer, et al., J. Exp. Med. 176:1007 (1992); and J. Hammer, et al., PNAS U.S.A. 91:4456 (1994)). The methods disclosed herein are used to compute the change in affinity due to these mutations.

The novel strategy disclosed herein for ligand design is to start with a given conformation of receptor (or other target molecule, such as an antibody or an enzyme) and find the properties of the ligand that will optimally complement that conformation. The tests performed described herein assay whether the methods can detect differences in affinity due to differences in the ligand charge distribution, an essential prerequisite for defining the optimal ligand charge distribution. When the point-charge magnitudes are optimized as described in the previous paragraph, it is expected that the polarity assigned to the Tyr1 hydroxyl remains, that of Val2 increase, and that of Gln4 and Thr6 decrease, reflecting the electrostatic tendencies of Hammer et al. (J. Hammer, et al., J. Exp. Med. 176:1007 (1992); and J. Hammer, et al., PNAS U.S.A. 91:4456 (1994)).

Pattern of Polar and Non-Polar Side Chains

The methods of the present computer-implemented process are used to probe the peptide binding site without reference to known positions of peptide atoms. This probing is done in two modes. In one mode, each of the five major binding pockets is probed through individual optimization of the charge distribution in that site only; in the second, the five major binding pockets are probed together, with the charge distribution for the entire site optimized in one computation. A comparison of the results indicates the extent to which the sites are coupled; experimental work suggests that the coupling should be minimal (J. Hammer, et al., J. Exp. Med. 180:2353 (1994)). A complementary shaped region is constructed through sphere packing and the multipolar charge distribution that optimizes binding to the site is computed. Both through direct examination of the multipoles and by constructing a gridded point-charge distribution complementary to the site, each site is categorized as to how well it accepts hydrophobic, polar, positive, and negative groups. Examination may reveal mixed character, where a site is largely hydrophobic but accepting of some localized polar groups (presumably the Tyr1 site is of this type). Comparison with the known site characteristics is done to evaluate the results. A discrepancy may result if the peptide desolvation penalty used in the computation (that which would result from a rigid peptide in the bound conformation) were substantially different from that experienced by actual ligands in phage-display studies. However, we do not anticipate this discrepancy to be of concern because the desolvation penalty is dominated by polar and charged groups, which should be exposed to solvent in the unbound state and which should be in the observed extended and twisted conformation.

Backbone Trace and Contacts

Because the backbone trace is thought to be invariant for essentially all peptides that bind, one expects the site to strongly dictate backbone contacts. Accordingly, the methodology of the present computer-implemented process is used to regenerate the position of the backbone observed crystallographically to further validate the methods disclosed herein. Using the above-described methods, the distributed multipole description of the optimal ligand in the region of peptide backbone binding is identified, converted to a gridded point-charge field, and the peptide amide groups (N-methyl acetamide) are fitted into the charge field as a least-squares fit while also not allowing steric overlap with the walls of the site.

Design for Enhanced Binding

In general terms, the strategy for designing enhanced binding ligands is used to locate opportunities where known ligands do not take full advantage of the site. To this end, both individual chemical groups that pay more in desolvation energy than they recover in favorable interactions and also sites where current liganding groups fall short of computed optima are identified. The computations carried out above (Testing and Validation) are re-analyzed in search of such opportunities.

Analysis of Bound-Peptide Complex

The complete electrostatic dissection described above is used to detect functional groups (side chains or backbone dipolar groups on both the peptide and the binding site) whose total electrostatic contribution to binding is unfavorable (that is, whose mutation to a hydrophobic group is computed to lead to tighter binding). This electrostatic dissection suggests targeting regions of the peptide (even if they are backbone) for modification to hydrophobic groups to produce a more stable complex. Using this strategy we were able to identify three stabilizing mutations in a variant of the Arc repressor (Z. S. Hendsch, et al., Biochemistry 35:7621 (1996)). An MHC protein group that contributes unfavorably to binding can be ameliorated by modifying the peptide to make improved interactions with it. These opportunities can be confirmed by a number of parallel studies, including the computation in which the point charges of the viral peptide atoms are re-optimized (see above). The same locations for reduction and increase in the polarity of the ligand should be found. Such parallel confirmation is used to provide further evidence that a proposed site can be modified to enhance binding.

Pattern of Polar and Non-Polar Side Chains

It is anticipated that the individual pocket optimizations as well as that of the whole site can be used as the source of suggested detailed changes for the purpose of identifying ligands with enhanced binding to its target molecule. In choosing locations for such optimization, regions where the largest free energy gains can be recovered as measured by discrepancy between actual and optimized charge distribution and corresponding binding energy are initially selected. Three such regions include: the position 1 binding pocket, the peptide-backbone binding area (see below), and a pocket occupied by a solvent cluster in the viral-peptide study (L. J. Stem, et al., Nature (London) 368:215 (1994)). Position 1 accommodates a Tyr in the viral-peptide complex (L. J. Stem, et al., Nature (London) 368:215 (1994)) but is frequently found as Phe or Trp as well (J. Hammer, et al., J. Exp. Med. 176:1007 (1992); and J. Hammer, et al., PNAS U.S.A. 91:4456 (1994). In a recently determined crystal structure of HLA-DR1 with a different peptide bound, Trp occupies the site. The orientation of the Trp side chain is roughly 90° rotated with respect to the Tyr, yet the surrounding protein pocket is essentially unchanged. Placing a large hydrophobic side chain in this pocket appears virtually a requirement for binding J. Hammer, et al., PNAS U.S.A. 91:4456 (1994)). The optimized charge distribution generated for groups binding to this pocket can be used as a guide to a combinatorial synthetic scheme to synthesize enhanced binding ligands.

Backbone Trace and Contacts

The present computer-implemented process can be used to design ligands having non-peptide backbones for improved binding. By comparing the optimized charge distributions for the backbone-binding region to the peptide charge distribution, improved backbone chemistries can be rationally designed. For example, the method can be used to identify ligands that have the equivalent of an alpha-carbon (or at least a beta-carbon) so permit attachment of the presented side chains onto the T-cell side of any new platform is designed.

EXAMPLE 2

HIV Protease

Introduction

The protease from HIV is required for proper assembly of virus. Inactivation of the protease by mutation leads to the production of non-infectious particles. Design of HIV-protease inhibitors has been a major effort of a number of pharmaceutical companies for the past decade or more. This research was aided by the facility with which high-resolution X-ray crystallographic data could be obtained after proper conditions were worked out for expression, purification, and crystallization. In the Protein Data Bank there are currently over 45 structures of HIV-1 protease either alone or in complex with ligand. These structures provide a rich data set for examining modes of interaction of different ligands with a common protein. A number of very promising inhibitors have already been developed, some are in clinical trials, and a few have been approved by the FDA. Nevertheless, "escape" mutants of the protease have been isolated for a number of these inhibitors.

The protease structure reveals an essentially symmetric homodimer of a 99-residue polypeptide chain. The active site is formed at the two-fold axis, is enclosed by a pair of symmetry-related loops that appear highly flexible in the unbound state but close over the active site upon ligand binding, and adjoins a cleft that can bind substrates up to seven residues long. The active site contains the triad Asp25, Thr26, and Gly27 from each subunit, with the pair of Asp25 carboxylate groups in close proximity and nearly coplanar. The apparent exact two-fold symmetry of the enzyme in the absence of ligand is disrupted somewhat by binding (asymmetric) peptide ligands. One particularly interesting issue in design studies has been whether asymmetric ligands (such as those modeled on peptide substrates) or symmetric ligands (which have the opportunity to bind with the ligand two-fold axis coincident with the enzyme two-fold) are tighter binding. A surprising result has been that certain symmetric ligands are found to bind asymmetrically in the active site. The computational methods disclosed herein can be used to investigate the energetic contributions to this difference.

Substrate specificity studies have been used to determine binding preferences for peptides. These have revealed affinity for Gln or Glu at the P2' position and a largely hydrophobic side chain (Phe, Leu, Met, Asn, or Tyr) at P1. Less pronounced preferences include Glu at P3 and a hydrophobe at P2 (A. Wlodawer and J. W. Erickson, Annu. Rev. Biochem. 62:543 (1993)).

The application of the methods disclosed herein to the analysis of binding modes of molecules whose involvement is critical to HIV infection can be used to facilitate the design of tight-binding ligand molecules for use as diagnostic and therapeutic agents. In general, the methods of the present computer-implemented process are primarily continuum electrostatics and secondarily free energy simulations. The process provides a novel method for finding the electrostatic complement of a target molecule. The preliminary results demonstrate that the computational modeling used herein for molecular and energetic dissection for a continuum analysis yield conclusions that are consistent with those found in by using a more detailed (and time-consuming) free energy simulation for a pair of studies on protein-DNA recognition by 434 repressor (see, example 3).

Testing

Initial testing of the fundamentals of the method are carried out in studies of the class II MHC molecule, and next carried out using the HIV-1 protease. Accordingly, the above-described methods are used to design enhanced-binding ligands that bind to the HIV-1 protease. One difficulty encountered with many ligand design protocols is the need to predict the conformation of bound complexes. The present computer-implemented process circumvents this problem by choosing a conformation of the protein and solving for a set of molecular descriptors for an optimally complementary ligand. The process also provides tools to examine a subset of the available structures of HIV-1 protease, both alone and in complex with various ligands.

Loop Conformation

Two symmetry related loops are in an open conformation in the unbound form of the enzyme and close down against the active site in the bound form. One set of inhibitors that is well characterized and is attractive due to their relative rigidity is the cyclic urea compounds being developed by DuPont Merck Pharmaceuticals (P. Y. S. Lam, et al., Science 263:380 (1994) and C. N. Hodge, et al., Chem. & Biol. 3:301 (1996)). Members of this family of compounds can be used to analyze the bound-state structure. For example, the complex with XK 263 (a symmetric cyclic urea with two naphthyl, two phenyl, and two hydroxyl substituents) is in the Protein Data Bank, and the complexes with DMP 323 and DMP 450 are shown in FIG. 4 ("Inhibitors of HIV-1 Protease"). The effect of this conformational change is examined on the computed properties of the optimal ligand using the above-described methods. The effect of receptor conformational change on complementary ligand properties is examined by characterizing the optima by the shapes and relative polarities of the moieties occupying individual subsite pockets at the active site. It is anticipated that the differences in computations will be rather small, since the substrate must initiate binding with the loops in the open conformation and complete binding when the loops are closed. Substrates either represent some compromise between being complementary to the open and closed form, or there isn't substantial difference between the two.

Protonation State

One important and currently unresolved question central to the design of protease inhibitors is the protonation state of the catalytic aspartyl residues (Asp 25 and 25'). It is anticipated that the protonation state of this pair of side chains will substantially change the properties of the computed electrostatic complement. It is potentially worthwhile for a ligand to incur greater desolvation penalty to interact with a charged, rather than an uncharged, aspartic acid. It is anticipated that a comparison of the computed optimal ligand electrostatic properties to actual bound ligands will permit the assignment of protonation states to some of these complexes. The case of the cyclic ureas from the DuPont Merck group are useful in this study because NMR evidence is consistent with the aspartyl groups each being protonated (D. A.

Torchia, et al., J. Am. Chem. Soc. 116:1149 (1989)). By comparing the optimal complements from computations using a doubly-, singly-, and unprotonated catalytic pair, the affect of the availability of chemical freedom in an active site on its ligand binding properties is determined. Such studies also permit the identification of a preferred titration state that is more susceptible to ligand binding than others.

Symmetric and Asymmetric Binding

A number of symmetric inhibitors have been designed based on the principle that they would be more complementary to the symmetric enzyme (M. Miller, et al., Science 246:1149 (1989)). Although some of these have been observed to binding symmetrically in crystallographic studies (XK 263 (P. Y. S. Lam, et al., Science 263:380 (1994), DMP 450 (C. N. Hodge, et al., Chem. & Biol. 3:301 (1996)), and A-76928 (M. V. Hosur, et al., J. Am. Chem. Soc. 116:847 (1994)), others bind asymmetrically (A-76889 (M. V. Hosur, et al., J. Am. Chem. Soc. 116:847 (1994)). There could be two reasons for asymmetric binding of a symmetric inhibitor. Either the site can deform so that it is truly complementary to an asymmetric ligand, or the site can remain essentially symmetric but the ligand preferentially makes asymmetric interactions. These cases can be distinguished more precisely by examining the computed electrostatic complement for sites harboring symmetrically and asymmetrically bound ligands for two-fold symmetry. If the complement remains symmetric for asymmetrically bound ligands, improvements to the ligand can be defined using the above-described methods. For example, enhanced-binding ligands can be designed by studying the four compounds in FIG. 4 which represent different choices (both symmetric and asymmetric) for using hydroxyl groups to compensate the buried catalytic aspartic acid side chains.

Design

The approaches to design of protease inhibitors are similar to those described above in reference to the design of MHC ligands. A few design points unique to HIV protease are described herein.

Each of the above-described studies answers specific questions about how conformational and titration changes to active sites affect the properties of the computed complementary ligand. Each study also can be analyzed for opportunities to modify existing ligands (to obtain "enhanced-binding ligands") or to design entirely new ligands with enhanced affinity. Alcohols and diols are prevalent in a number of HIV-1 protease inhibitors; more effective moieties to satisfy the electrostatic properties of the aspartyl groups can be identified to design enhanced-binding ligands.

One particularly important problem with all drugs targeted to HIV is the eventual evolution of "escape" mutants.

The invention is useful for developing the minimal charge configuration required to complement the active site residues. It is believed that such a core molecule is useful because its limited size should reduce the number of contacts potentially disruptable by escape mutants. In addition, since contacts would all be at the catalytic site, disrupting mutants could be inactive.

Design Studies on Other HIV Targets

Design studies against other HIV targets are performed using the above-described methods. Other HIV targets include the RNA complexes of TAR and RRE and the HIV envelope proteins.

EXAMPLE 3

The 434 Repressor DNA-binding Domain

Introduction

We have analyzed the high-resolution X-ray crystal structure of the 434 repressor DNA-binding domain, R1-69, bound to the $O_R1$ operator using continuum electrostatic calculations. The principal results are outlined below. The interaction was dissected into contributions from each protein backbone carbonyl, $C_\alpha NH$, and side chain and each nucleic-acid ribose, base, and phosphate. For each group a desolvation contribution to binding was calculated as well as contributions from new interactions made across the interface (termed "intermolecular") and from changes in the screening within the protein or DNA (termed "intramolecular" interactions).

Currently only the rigid binding of pre-conformed protein dimer to pre-conformed DNA has been studied. These methods can be extended to address conformational flexibility as described above. The overall electrostatic contribution to binding is unfavorable (45.3 kcal/mol). This is due to a large desolvation penalty (132.9 kcal/mol) that is only partially offset by favorable intermolecular terms (−96.4 kcal/mol). The sum of intramolecular terms is small and unfavorable (8.8 kcal/mol). Four salt bridges formed in the complex (two symmetry-related pairs) stabilize complex formation by an average of −1.7 kcal/mol each. This is due largely to the fact that these groups incur a smaller desolvation penalty than do protein side chains in folding from the unfolded state. In this regard, binding appears to be somewhat different from folding, but our further results show that the distinction is somewhat more complex.

The largest contributors to the desolvation penalty come from the charged groups in the system—protein side chains (63.5 kcal/mol) and DNA backbone groups (50.6 kcal/mol). Protein backbone groups (6.9 kcal/mol) and DNA bases (11.9 kcal/mol) incur much smaller costs. The desolvation penalty is substantial for many groups that become buried at the protein-DNA interface. Interestingly, some side chains that lie nearby but not at the interface also lose significant solvation on binding.

The strong, favorable intermolecular interactions formed in the complex are made almost entirely with DNA backbone groups. Surprisingly, equal amounts come from interactions with protein side chains (−42.2 kcal/mol), which include a large number of charged groups, as with the protein backbone (−41.8 kcal/mol), which is only polar except for the charged termini. The analysis points to strong interactions made between the N-termini of alpha-helices and individual phosphate groups as well as the strong interaction between the backbone groups in a protein loop with a set of phosphates. Additionally, some interactions between charged side chains and the DNA backbone are rather distant, but are directed through the low-dielectric protein, where electrostatic interactions might be expected to be longer range due to less screening by solvent.

Intermolecular interactions with the bases are small: 2.2 kcal/mol (unfavorable) with protein backbone and −14.6 kcal/mol (favorable) with protein side chains, although the base-side chain interactions are generally thought to confer substantial specificity to protein-DNA complexes. Interestingly, interactions close enough to make a hydrogen bond account for roughly half the favorable intermolecular interactions; an equal contribution comes from interactions too distant to be hydrogen bonding. In particular, many of these more distant interactions are to the "non-contacted" bases in the central region of the operator; Arg43 in the left and right half-sites contribute −3.9 kcal/mol.

Overall the intramolecular interactions contribute only 8.8 kcal/mol to the electrostatic docking energy, but the sources of this effect are quite interesting. These interactions exist in the identical geometry in the bound and free states since they are within the protein or DNA. Their magnitude changes on docking, however, because the removal of high-dielectric solvent in the complex reduces the screening of interactions. Repulsions within the DNA backbone (due largely to phosphate-phosphate interactions) increase in magnitude by 19.2 kcal/mol on binding protein because the reduced solvent screening in the bound state leads to a lower effective dielectric. This is partially offset by a favorable contribution between protein side chains of −11.9 kcal/mol, which is due largely to attractive salt bridges within the protein whose strength "increases" due to reduced screening in the complex.

When all of the contributions (desolvation, intermolecular, and intramolecular) are tabulated for each group, most groups individually pay more in desolvation energy than they recover in other interactions. This is particularly true for the phosphate groups and all but one base, as well as for the side chains at the binding interface. Groups that do recover more than they pay in desolvation energy tend to be largely buried in the undocked state.

In summary, this work demonstrates the detailed insights that result from an energetic dissection of a binding event. These techniques are useful for exploring ligand binding to HIV targets, and permit the rational design of enhanced-binding ligands.

Free Energy Analysis of the Effect of a Point Mutation: Simulation of a Base-Pair Change in a 434 Repressor-DNA Complex To address specific issues of recognition and to validate the results of our continuum electrostatic investigation, we carried out a free energy simulation study with explicit solvent. The bound-state starting structure was the high-resolution complex of R1-69 bound to $O_R2$ (L. J. W. Shimon and S. C. Harrison, J. Mol. Biol. 232:826–838 (1993)). The mutation was TA→GC at position 7L. Multiple unbound conformations of the DNA were generated from a 300-ps molecular dynamics trajectory. Five frames of the trajectory were chosen and used as starting structures for the unbound-state free energy calculation. Although most of the interactions between 434 repressor and DNA are in the major groove, this operator mutation occurs near the pseudo-dyad axis where repressor faces the minor-groove side of DNA. A total of ten simulations were carried out in the unbound state and six in the bound state, which led to good statistics. The results are outlined briefly here (E. J. Simon, "A Molecular Dynamics Study of a Mutation in a Bacteriophage 434 Operator/Repressor Complex", PhD thesis, Harvard University (1996)).

Results:

The overall stability change is +1.4±0.7 kcal/mol, which disfavors binding to the mutant operator. This is in good agreement with experimental values of 0.8–1.2 kcal/mol (G. B. Koudelka, et al., Nature (London) 326:886 (1987)). An analysis of the source of this overall stability change (B. Tidor, "Molecular Modeling of Contributions to Free Energy Changes: Applications to Proteins. PhD thesis, Harvard University (1990); B. Tidor and M. Karplus, Biochemistry 30:3217 (1991); and B. Tidor Proteins: Struct., Funct., Genet. 19:310 (1994)) was carried out and shows a strong repulsion between the side chain of Arg43L and the N2 amino group of the mutant guanine. This is a remarkably interesting interaction because it suggests that this arginine acts as a negative determinant of specificity by "interfering" with a guanine at this position. The array of hydrogen-bond acceptors in the minor groove in this AT-rich region of the mutation site and the flanking phosphate groups polarize the surrounding solvent water to interact favorably with this negative potential. The introduction of the Gua N2 donor to the minor groove effectively repels this polarized solvent. The repulsion is stronger in the unbound than the bound state because solvent is displaced from this region of the minor groove on protein binding.

Comparison of these free energy simulation results with the continuum electrostatic study shows essentially the same dissection for the interactions of Arg 43, including the solvent polarization effect. This comparison demonstrates the accuracy of continuum methodology relative to explicit simulations. The present computer-implemented process is based around the continuum approach, which is more economical and can be used to analyze an entire binding site at once, rather than one group at a time. Free energy simulations are used primarily to examine points of disagreement between continuum theory and experiment.

APPENDIX

Figure 5A:
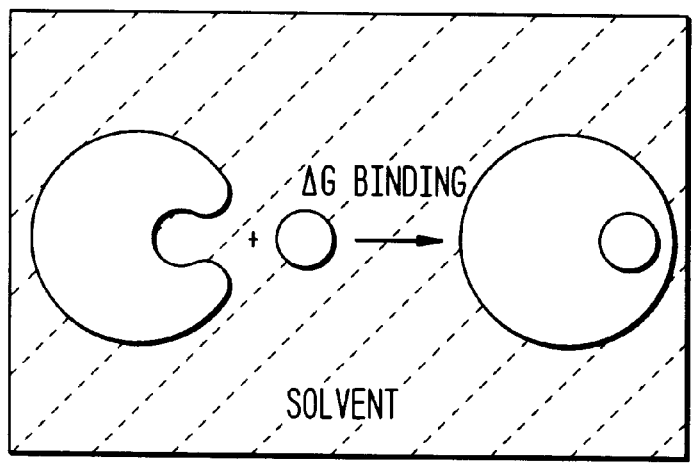
FIG. 5 is an illustration of problem geometries.
Figure 5B:
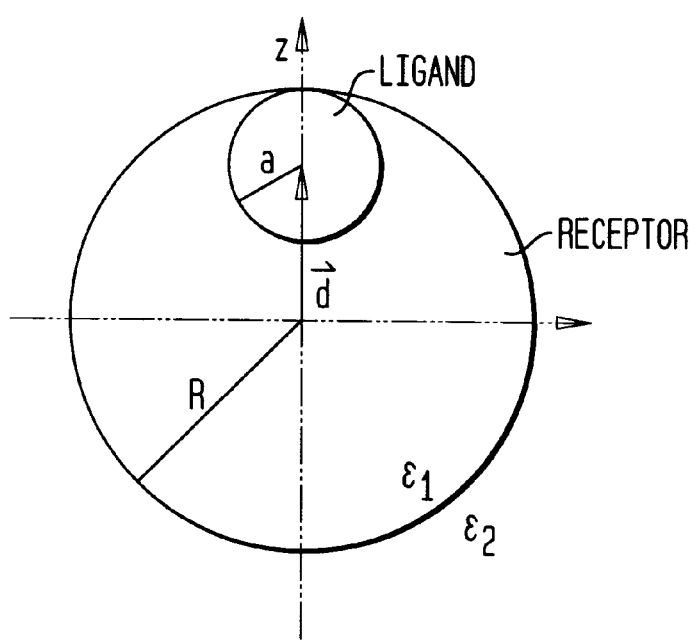

FIG. 5. illustrates problem geometries. FIG. 5a. shows the binding reaction between a receptor (R) and spherical ligand (L) that dock rigidly to form a spherical bound-state complex. Receptor, ligand, and complex are all low-dielectric media ($\in_1$) that are surrounded by high-dielectric solvent ($\in_2$). FIG. 5b. shows that the boundary-value problem solved here involves a charge distribution in a spherical region of radius R with dielectric constant $\in_1$ surrounded by solvent with dielectric constant $\in_2$. The origin of coordinates is the center of the larger spherical region, but the charge distribution is expanded in multipoles about a point a distance d along the z-axis. The geometric requirement is that the ligand sphere not extend beyond the receptor sphere, $R \geq d+a$, although the case of equality is illustrated in the figure.

The electrostatic free energy of binding is the difference between the electrostatic free energy in the bound and the unbound state, $\Delta G_{binding} = G^{bound} - G^{unbound}$ (see FIG. 5a). Because the dielectric model includes responses that affect the entropy as well as the en-thalpy, the electrostatic energy is considered to be a free energy. The free energy of each state is expressed as a sum of coulombic and reaction-field (hydration) terms involving the ligand (L), the receptor (R), and their interaction (L–R):

$$G^{state} = G_{coul,L}^{state} + G_{coul,R}^{state} + G_{coul,L-R}^{state} + G_{hyd,L}^{state} + G_{hyd,R}^{state} + G_{hyd,L-R}^{state}. \quad (1)$$

This results in the following expression for the binding free energy, $$\Delta G_{binding} = \Delta G_{coul,L-R} + \Delta G_{hyd,L-R} + \Delta G_{hyd,L} + \Delta G_{hyd,R} \quad (2)$$

where the fact that the geometry of point charges in the receptor and ligand remain fixed is used in the model to cancel the coulombic self contribution of ligand and receptor and where the two L–R terms are due only to the bound state because the ligand and receptor are assumed not to interact in the unbound state. (Note, however, that the charge distribution for the receptor need not be the same in the bound and unbound states. If they are different, this adds a constant to $\Delta G_{binding}$ that can be dropped in defining $\Delta G_{var}$ in Eq. (3)). Thus, Eq. (2) describes the electrostatic binding free energy as a sum of desolvation contributions of the ligand and the receptor (which are unfavorable) and solvent-screened electrostatic interaction in the bound state (which is usually favorable). Since the goal is to vary the ligand charge distribution to optimize the electrostatic binding free energy and the last term simply adds a constant, a relevant variational binding energy is defined, $$\Delta G_{var} = \Delta G_{int,L-R} + \Delta G_{hyd,L} \quad (3)$$

in which the first two terms on the right hand side (RHS) of Eq. (2) have been combined into a screened interaction term and the constant term has been dropped. Note that $$\Delta G_{int,L-R} = \sum_{j \in R} q_j V_L^{bound}(\vec{r_j}) = \sum_{j \in R} q_j [V_{coul,L}^{bound}(\vec{r_j}) + V_{hyd,L}^{bound}(\vec{r_j})] \quad (4)$$

and $$\Delta G_{hyd,L} = \frac{1}{2} \sum_{i \in L} q_i V_{hyd,L}^{bound}(\vec{r_i}) - \frac{1}{2} \sum_{i \in L} q_i V_{hyd,L}^{unbound}(\vec{r_i}) \quad (5)$$

where $V_L^{state}$ is the total electrostatic potential in the indicated state due to the ligand charge distribution only and $V_{term,L}^{state}$ is the coulombic or reaction-field (hydration) term, as indicated. The summations are over atomic point charges in the ligand ($i \in L$) or receptor ($j \in R$). The factor of ½ in Eq. (5) is due to the fact that the ligand charge distribution interacts with the self-induced reaction field. $V_{coul,L}^{bound}$, $V_{hyd,L}^{bound}$, and $V_{hyd,L}^{unbound}$, the three electrostatic potentials in Eqs. (4) and (5), are expressed in terms of the given geometry and charge distribution by solving the boundary-value problem shown in FIG. 5b. A charge distribution (corresponding to the ligand) is embedded in a sphere of radius R. The center of the sphere is taken as the origin of coordinates (unprimed) but the charge distribution in multipoles is expanded about a second origin (primed) translated a distance d along the z-axis, so that $$\vec{r}(r,\theta,\phi) = \vec{d}(d, \theta_d = 0, \phi_d = 0) + \vec{r}'(r',\theta',\phi'). \quad (6)$$

The potential everywhere satisfies the Poisson equation. Inside the sphere, it may be written as, $$V_{in}(\vec{r}) = \sum_i \frac{q_i}{\epsilon_1 |\vec{r} - \vec{r_i}|} + \sum_{l=0}^{\infty} \sum_{m=-l}^{l} A_{l,m} r^l Y_{l,m}(\theta, \phi) \tag{7}$$

where the first term on the RHS is the coulombic and the second is the reaction-field (hydration) potential, and the summation over i corresponds to the ligand point charges. Outside the sphere, the coulombic and reaction-field potential can be combined and written as, $$V_{out}(\vec{r}) = \sum_{l=0}^{\infty} \sum_{m=-l}^{l} \frac{B_{l,m}}{r^{l+1}} Y_{l,m}(\theta, \phi) \tag{8}$$

where $A_{l,m}$ and $B_{l,m}$ are to be determined by the proper boundary conditions and $Y_{l,m}(\theta, \phi)$ are the spherical harmonics. The coulombic term in Eq. (7) is expanded in spherical harmonics and multipoles of the charge distribution about the center of the sphere. Here the origin of the multipole expansion is shifted to $\vec{d}$, $$\sum_i \frac{q_i}{\epsilon_1 |\vec{r} - \vec{r_i}|} = \sum_i \frac{q_i}{\epsilon_1 |(\vec{r} - \vec{d}) - \vec{r_i}'|} = \sum_i \frac{q_i}{\epsilon_1 |\vec{r}' - \vec{r_i}'|} \tag{9}$$

$$= \sum_{l=0}^{\infty} \sum_{m=-l}^{l} \frac{4\pi}{2l+1} Q'^*_{l,m} \frac{Y_{l,m}(\theta', \phi')}{\epsilon_1 r'^{l+1}} \tag{10}$$

where $Q'_{l,m}$ is a spherical multipole expanded about the primed origin, $\vec{d}$, $$Q'^*_{l,m} \equiv \sum_i q_i r_i'^l Y^*_{l,m}(\theta_i', \phi_i'). \tag{11}$$

The definition of the $Y_{l,m}(\theta, \phi)$ used by Jackson[1] is adopted. The expression in Eq. (10) is valid for $r' > r'_i$ (i.e., outside the ligand or, more precisely, outside the sphere whose center is at $\vec{d}$ and whose radius is the longest distance between $\vec{d}$ and a point charge).

To substitute into Eq. (7) and combine terms involving spherical harmonics, first $Y_{l,m}(\theta', \phi')/r'^{l+1}$ of Eq. (10) is expanded in terms of $Y_{l,m}(\theta, \phi)/r^{l+1}$. This is done using the results of Greengard,[2] which state that for $r > d$, $$\frac{Y_{l,m}(\theta', \phi')}{r'^{l+1}} = \sum_{l'=0}^{\infty} \sum_{m'=-l'}^{l'} K_{l',m',l,m} \left[\frac{4\pi(2l+1)}{(2l'+1)(2l'+2l+1)}\right]^{\frac{1}{2}} \tag{12}$$

$$d^{l'} Y^*_{l',m'}(\theta_d, \phi_d) \frac{Y_{l'+l,m'+m}(\theta, \phi)}{r^{l'+l+1}}$$

where $$K_{l',m',l,m} = \left[\frac{(l'+l+m'+m)!(l'+l-m'-m)!}{(l'+m')!(l'-m')!(l+m)!(l-m)!}\right]^{\frac{1}{2}}. \tag{13}$$

Since a geometry with $\theta_d = 0$ (FIG. 1b) has been used, only $m' = 0$ terms in Eq. (12) are non-vanishing, in which case Eq. (10) becomes, $$\sum_i \frac{q_i}{\epsilon_1 |\vec{r} - \vec{r_i}|} = \sum_{l=0}^{\infty} \sum_{m=-l}^{l} \frac{1}{\epsilon_1} \left(\frac{4\pi}{2l+1}\right)^{\frac{1}{2}} \tag{14}$$

$$Q'^*_{l,m} \sum_{l'=0}^{\infty} K_{l',0,l,m} d^{l'} \left(\frac{4\pi}{2l'+2l+1}\right)^{\frac{1}{2}} \frac{Y_{l'+l,m}(\theta, \phi)}{r^{l'+l+1}}$$

in which the multipole distribution is taken about the point $\vec{d}$, but the potential is expressed as a summation of spherical harmonics about the large-sphere center. The above equation can also be written as, $$\sum_i \frac{q_i}{\epsilon_1 |\vec{r} - \vec{r_i}|} = \tag{15}$$

$$\sum_{l=0}^{\infty} \sum_{m=-l}^{l} \frac{1}{\epsilon_1} \left(\frac{4\pi}{2l+1}\right)^{\frac{1}{2}} \frac{Y_{l,m}(\theta, \phi)}{r^{l+1}} \sum_{l'=|m|}^{l} K_{l-l',0,l',m} d^{l-l'} \left(\frac{4\pi}{2l'+1}\right)^{\frac{1}{2}} Q'^*_{l',m}$$

where terms with the same $Y_{l,m}(\theta, \phi)$ are grouped together, as opposed to Eq. (14), where terms with the same $Q'^*_{l,m}$ are grouped.

Upon substituting Eq. (15) into Eq. (7) and matching boundary conditions at $r = R$, $$V_{in}|_{r=R} = V_{out}|_{r=R} \tag{16}$$

$$\epsilon_1 \frac{\partial V_{in}}{\partial r}\bigg|_{r=R} = \epsilon_2 \frac{\partial V_{out}}{\partial r}\bigg|_{r=R} \tag{17}$$

the hydration (reaction-field) potential inside the sphere is, $$V_{hyd}(\vec{r}) = \sum_{l=0}^{\infty} \sum_{m=-l}^{l} A_{l,m} r^l Y_{l,m}(\theta, \phi) \tag{18}$$

$$= \sum_{l=0}^{\infty} \sum_{m=-l}^{l} \left(\frac{4\pi}{2l+1}\right)^{\frac{1}{2}} r^l Y_{l,m}(\theta, \phi) \left(\frac{C_l}{R^{2l+1}}\right)$$

$$\sum_{l'=|m|}^{l} K_{l-l',0,l',m} d^{l-l'} \left(\frac{4\pi}{2l'+1}\right)^{\frac{1}{2}} Q'^*_{l',m} \tag{19}$$

where $$C_l = \frac{(\epsilon_1 - \epsilon_2)}{\epsilon_1 [\epsilon_2 + l\epsilon_1/(l+1)]}. \tag{20}$$

The various V's can be rewritten, with their dependence on the $Q'^*_{l,m}$ made explicit. $V'^{bound}_{coul,L}$ is given by Eq. (10), $V^{bound}_{hyd,L}$ is given by Eq. (19) but rewritten so that the terms with the same $Q'^*_{l,m}$ are collected, and $V^{unbound}_{hyd,L}$ is given by Eq. (19) with $R = a$ and $d = 0$.

$$V'^{bound}_{coul,L}(\vec{r}') = \sum_{l=0}^{\infty} \sum_{m=-l}^{l} \frac{4\pi}{2l+1} Q'^*_{l,m} \frac{Y_{l,m}(\theta', \phi')}{\epsilon_1 r'^{l+1}} \tag{21}$$

$$V_{hyd,L}^{bound}(\vec{r}) = \sum_{l=0}^{\infty}\sum_{m=-l}^{l}\sum_{l'=l}^{\infty}\left(\frac{4\pi}{2l+1}\right)^{\frac{1}{2}}$$ (22)

$$\left(\frac{4\pi}{2l'+1}\right)^{\frac{1}{2}} Q'^{*}_{l,m} K_{l'-l,0,l,m} d^{l'-l} \left(\frac{C_{l'}}{R^{2l'+1}}\right) r^{l'} Y_{l',m}(\theta,\phi)$$

$$V_{hyd,L}^{unbound}(\vec{r}) = \sum_{l=0}^{\infty}\sum_{m=-l}^{l} \frac{4\pi}{2l+1}\left(\frac{C_l}{\alpha^{2l+1}}\right) Q'^{*}_{l,m} r^l Y_{l,m}(\theta,\phi)$$ (23)

Substituting into Eq. (4), the dependence of $\Delta G_{int,L-R}$ on the $Q'^*_{l,m}$ is made explicit, $$\Delta G_{int,L-R} = \sum_{j \in R} q_j \left[ V_{coul,L}^{bound}(\vec{r}_j) + V_{hyd,L}^{bound}(\vec{r}_j) \right]$$ (24)

$$= \sum_{l=0}^{\infty}\sum_{m=-l}^{l} Q'^*_{l,m} \sum_{j \in R} q_j \left[ \left(\frac{4\pi}{2l+1}\right) \frac{Y_{l,m}(\theta'_j,\phi'_j)}{\epsilon_1 r_j^{l+1}} + \right.$$ (25)

$$\sum_{l'=l}^{\infty}\left(\frac{4\pi}{2l+1}\right)^{\frac{1}{2}}\left(\frac{4\pi}{2l'+1}\right)^{\frac{1}{2}} K_{l'-l,0,l,m} d^{l'-l}\left(\frac{C_{l'}}{R^{2l'+1}}\right)$$

$$\left. r_j^{l'} Y_{l',m}(\theta_j,\phi_j) \right]$$

$$\equiv \sum_{l=0}^{\infty}\sum_{m=-l}^{l} \alpha_{l,m} Q'^*_{l,m}$$ (26)

where in the last line the element $\alpha_{l,m}$ is defined, which is independent of the $Q'^*_{l,m}$, to be the factor multiplying $Q'^*_{l,m}$ in Eq. (25). Each $\alpha_{l,m}$ expresses the contribution of a multipole to $\Delta G_{int,L-R}$ and contains all information concerning the receptor charge distribution required to obtain $\Delta G_{var}$.

For $\Delta G_{hyd,L}$ it is useful to re-express Eq. (5) in terms of the $Q'^*_{l,m}$, the multipoles describing the ligand charge distribution, rather than the individual charges, $q_i$. $V(\vec{r})$ is expanded around the center of the multipole expansion, $\vec{d}$, $$\sum_{i \in L} q_i V(\vec{r}_i) = \sum_{i \in L} q_i V(\vec{d} + \vec{r}'_i)$$ (27)

$$= \sum_{i \in L} q_i \left[ V(\vec{d}) + \vec{r}'_i \cdot \vec{\nabla} V(\vec{d}) + ... \right].$$ (28)

It has been shown by Rose that in spherical coordinates the expansion becomes,[3]

$$\sum_{i \in L} q_i V(\vec{d}+\vec{r}'_i) = \sum_{l=0}^{\infty}\sum_{m=-l}^{l} \frac{4\pi}{(2l+1)!!} Q'^*_{l,m} y_{l,m}(\vec{\nabla}) V(\vec{d})$$ (29)

where $$y_{l,m}(\vec{r}) \equiv r^l Y_{l,m}(\theta,\phi)$$ (30)

and $y_{l,m}(\vec{\nabla})$ is the operator obtained by replacing $\vec{r}$ with $\vec{\nabla}$.

For positive m and when $y_{l,m}(\vec{\nabla})$ operates on a solution of the Laplace equation (i.e., $r^l Y_{l,m}(\theta,\phi)$ or $Y_{l,m}(\theta,\phi)/r^{l+1}$), it has been shown that,[3]

$$y_{l,m}(\vec{\nabla}) = \frac{(2l)!}{2^l l!}\left[\left(\frac{2l+1}{4\pi}\right)\frac{2^m}{(l+m)!(l-m)!}\right]^{\frac{1}{2}} \nabla_1^m \nabla_0^{l-m}$$ (31)

for $m \geq 0$.

The double-factorial is defined as $$(2l+1)!! = (2l+1)\cdot(2l-1)\cdot(2l-3)\ldots 3\cdot 1$$ (32)

$$= \frac{(2l+1)!}{2^l l!}$$ (33)

and the spherical partial derivatives are $$\nabla_1 = -\frac{1}{\sqrt{2}}(\nabla_x + i\nabla_y),\ \nabla_{-1} = \frac{1}{\sqrt{2}}(\nabla_x - i\nabla_y),\ \nabla_0 = \nabla_x.$$ (34)

To compute $y_{l,m}(\vec{\nabla})$ for negative m, the fact that $Y_{l,-m}(\theta,\phi)=(-1)^m Y^*_{l,m}(\theta,\phi)$ is used and the definitions of spherical partial derivatives in Eq. (34) to obtain, $$y_{l,-m}(\vec{\nabla}) = \frac{(2l)!}{2^l l!}\left[\left(\frac{2l+1}{4\pi}\right)\frac{2^m}{(l+m)!(l-m)!}\right]^{\frac{1}{2}} \nabla_{-1}^m \nabla_0^{l-m}$$ (35)

for $m \geq 0$.

The hydration energy of the bound ligand is then $$G_{hyd,L}^{bound} = \frac{1}{2}\sum_{i \in L} q_i V_{hyd,L}^{bound}(\vec{d}+\vec{r}'_i) = \frac{1}{2}\sum_{l'=0}^{\infty}\sum_{m'=-l'}^{l'} \frac{4\pi}{(2l'+1)!!} Q'^*_{l',m'} y_{l',m'}(\vec{\nabla}) V_{hyd,L}^{bound}(\vec{d})$$ (36)

$$= \frac{1}{2}\sum_{l'=0}^{\infty}\sum_{m'=-l'}^{l'} \frac{4\pi}{(2l'+1)!!} Q'^*_{l',m'} y_{l',m'} \sum_{l=0}^{\infty}\sum_{m=-l}^{l}\sum_{l''=l}^{\infty}\left(\frac{4\pi}{2l+1}\right)^{\frac{1}{2}}\left(\frac{4\pi}{2l''+1}\right)^{\frac{1}{2}} \times$$ (37)

$$Q'^*_{l,m} K_{l''-l,0,l,m} d^{l''-l}\left(\frac{C_{l''}}{R^{2l''+1}}\right) y_{l',m'}(\vec{\nabla})(r^{l''} Y_{l'',m}(\theta,\phi))\Big|_{\vec{r}=\vec{d}}.$$

To evaluate $y_{l,m}(\vec{\nabla})$ in Eq. (37), Eq. (31) and the gradient formula are used,[4]

$$\vec{\nabla}(\Phi(r)Y_{l,m}(\theta,\phi)) = -\left(\frac{l+1}{2l+1}\right)^{\frac{1}{2}}\left(\frac{d\Phi(r)}{dr} - \frac{l}{r}\Phi(r)\right)T_{l,l+1,m}(\theta,\phi) + \left(\frac{l}{2l+1}\right)^{\frac{1}{2}}\left(\frac{d\Phi(r)}{dr} + \frac{l+1}{r}\Phi(r)\right)T_{l,l-1,m}(\theta,\phi) \quad (38)$$

where $$T_{l,l',m}(\theta,\phi) \equiv \sum_{m'\in\{-1,0,1\}} C(l',1,l;m-m',m')Y_{l',m-m'}(\theta,\phi)\hat{\xi}_{m'} \quad (39)$$

the $C(l', 1, l; m-m', m')$ are the vector addition (or Clebsch-Gordon) coefficients frequently encountered in the study of angular momentum shown in Table I,[4] and $\hat{\xi}_m$, are spherical unit vectors, $$\hat{\xi}_1 = -\frac{1}{\sqrt{2}}(\hat{x}+i\hat{y}), \hat{\xi}_{-1} = \frac{1}{\sqrt{2}}(\hat{x}-i\hat{y}), \hat{\xi}_0 = \hat{z}. \quad (40)$$

Accordingly, $$\vec{\nabla} = \hat{x}\nabla_x + \hat{y}\nabla_y + \hat{z}\nabla_z = -\hat{\xi}_1\nabla_{-1} - \hat{\xi}_{-1}\nabla_1 + \hat{\xi}_0\nabla_0. \quad (41)$$

From Eqs. (38) through (41), $$\nabla_u(r^l Y_{l,m}(\theta,\phi)) = (-1)^u[l(2l+1)]^{1/2}C(l-1,1,l;m+u,-u)r^{l-1}Y_{l-1,m+u}(\theta,\phi) \quad (42)$$

Using Table I, Eq. (31), and Eqs. (37) through (42), the following intermediate results are obtained, $$\nabla_0^{l''-m'}(r^{l''}Y_{l'',m}) = \quad (43)$$

$$\left[\frac{(2l''+1)(l''+m)!(l''-m)!}{(2l''-2l'+2m'+1)(l''-m-l'+m')!(l''+m-l'+m')!}\right]^{\frac{1}{2}} r^{l''-l'+m'}Y_{l''-l'+m',m}$$

$$\nabla_1^{m'}(r^{l''-l'+m'}Y_{l''-l'+m',m}) = \quad (44)$$

$$(-1)^{m'}\left[\frac{(2l''-2l'+2m'+1)(l''-m-l'+m')!}{2^{m'}(2l''-2l'+1)(l''-m-l'-m')!}\right]^{\frac{1}{2}} r^{l''-l'}Y_{l''-l',m+m'}$$

$$\nabla_{-1}^{m'}(r^{l''-l'+m'}Y_{l''-l'+m',m}) = \quad (45)$$

$$(-1)^{m'}\left[\frac{(2l''-2l'+2m'+1)(l''+m-l'+m')!}{2^{m'}(2l''-2l'+1)(l''+m-l'-m')!}\right]^{\frac{1}{2}} r^{l''-l'}Y_{l''-l',m-m'}$$

and the final expression for the hydration energy of the ligand in the bound state, $$G_{hyd,L}^{bound} = \frac{1}{2}\sum_{i\in L} q_i V_{hyd,L}^{bound}(\vec{r_i}) = \frac{1}{2}\sum_{l=0}^{\infty}\sum_{m=-l}^{l}\sum_{l'=0}^{\infty}Q_{l,m}^{'*}Q_{l',m}'\sum_{l''=\max(l,l')}^{\infty}\left(\frac{4\pi}{2l+1}\right)^{\frac{1}{2}}\left(\frac{4\pi}{2l'+1}\right)^{\frac{1}{2}}\frac{C_{l''}}{R^{2l''+1}} \times \quad (46)$$

$$\frac{(l''+m)!(l''-m)!}{(l''-l)!(l''-l')!}\left[\frac{1}{(l+m)!(l-m)!(l'+m)!(l'-m)!}\right]^{\frac{1}{2}} d^{2l''-l-l'}$$

$$\equiv \sum_{l=0}^{\infty}\sum_{m=-l}^{l}\sum_{l'=0}^{\infty}\sum_{m'=-l'}^{l'}\beta_{l,m,l',m'}Q_{l,m}^{'*}Q_{l',m'}' \quad (47)$$

where $\beta_{l,m,l',m'}$ is defined by the above two equations; note that $\beta_{l,m,l',m'}$ is zero for m' m.

The hydration energy of the unbound ligand is obtained by setting d=0 and R=α in Eq. (46), $$G_{hyd,L}^{unbound} = \frac{1}{2}\sum_{i\in L} q_i V_{hyd,L}^{unbound}(\vec{r_i}) = \frac{1}{2}\sum_{l=0}^{\infty}\sum_{m=-l}^{l}\frac{4\pi}{2l+1}\left(\frac{C_l}{a^{2l+1}}\right)Q_{l,m}^{'*}Q_{l,m}' \quad (48)$$

$$\equiv \sum_{l=0}^{\infty}\sum_{m=-l}^{l}\gamma_{l,m}Q_{l,m}^{'*}Q_{l,m}' \quad (49)$$

where $\gamma_{l,m}$ is defined by Eqs. (48) and (49). Then, $\gamma_{l,m}$ is written as a function of both l and m for notational convenience, although there is no formal dependence on m.

Thus $\Delta G_{var}$ has been expressed as a function of the multipoles of the ligand charge distribution, $Q'_{l,m}$ (expanded about the center of the ligand sphere) and the elements $\alpha_{l,m}$, $\beta_{l,m,l',m'}$ and $\gamma_{l,m}$ which do not depend on $Q'_{l,m}$. Combining Eqs. (26), (47), and (49) gives $$\Delta G_{var} = \sum_{l=0}^{\infty}\sum_{m=-l}^{l}\alpha_{l,m}Q_{l,m}^{'*} + \quad (50)$$

$$\sum_{l=0}^{\infty}\sum_{m=-l}^{l}\sum_{l'=0}^{\infty}\sum_{m'=-l'}^{l'}\beta_{l,m,l',m'}Q_{l,m}^{'*}Q_{l',m'}' - \sum_{l=0}^{\infty}\sum_{m=-l}^{l}\gamma_{l,m}Q_{l,m}^{'*}Q_{l,m}'.$$

Note that only the $\alpha_{l,m}$ depend on the receptor charges, while the $\beta_{l,m,l',m'}$ and $\gamma_{l,m}$ depend solely on the geometry of the bound and unbound states. While $\Delta G_{var}^{opt}$ is a real quantity, the $\alpha_{l,m}$ and $Q'_{l,m}$ are complex and the products $\alpha_{l,m}Q'^*_{l,m}$ and $Q'^*_{l,m}Q'_{l',m}$ involve summations over terms of the form $Y^*_{l',m}(\theta',\phi')Y_{l,m}(\theta,\phi)$; note that the $\beta_{l,m,l',m'}$ and $\gamma_{l,m}$ are real. Then $\Delta G_{var}^{opt}$ is rewritten in terms of the real and imaginary parts of $\alpha_{l,m}$ and $Q'_{l,m}$, $$\Delta G_{var} = \sum_{l=0}^{\infty}\left[\alpha_{l,0}Q'_{l,0} + 2\sum_{m=1}^{l}(\text{Re}\alpha_{l,m}\text{Re}Q'_{l,m} + \text{Im}\alpha_{l,m}\text{Im}Q'_{l,m})\right] + \quad (51)$$

$$\sum_{l=0}^{\infty}\sum_{l'=0}^{\infty}\left[\beta_{l,0,l',0}Q'_{l,0}Q'_{l',0} + 2\sum_{m=1}^{l}\beta_{l,m,l',m}(\text{Re}Q'_{l,m}\text{Re}Q'_{l',m} + \text{Im}Q'_{l,m}\text{Im}Q'_{l',m})\right] -$$

$$\sum_{l=0}^{\infty}\left[\gamma_{l,0}Q'^2_{l,0} + 2\sum_{m=1}^{l}\gamma_{l,m}(\text{Re}Q'^2_{l,m} + \text{Im}Q'^2_{l,m})\right]$$

(where the summations over m are excluded for l=0) by noting again that $Y_{l,-m}(\theta,\phi) = (-1)^m Y^*_{l,m}(\theta,\phi)$ and $$Y^*_{l,m}(\theta',\phi')Y_{l,m}(\theta,\phi) + Y^*_{l,-m}(\theta',\phi')Y_{l,-m}(\theta,\phi) = Y^*_{l,m}(\theta',\phi')Y_{l,m}(\theta,\phi) + Y_{l,m}(\theta',\phi')Y^*_{l,m}(\theta,\phi) \quad (52)$$

$$= 2[\text{Re}Y_{l,m}(\theta',\phi')\cdot\text{Re}Y_{l,m}(\theta,\phi) + \text{Im}Y_{l,m}(\theta',\phi')\cdot\text{Im}Y_{l,m}(\theta,\phi)]. \quad (53)$$

The new variables $\text{ReQ}'_{l,m}$ and $\text{ImQ}'_{l,m}$ are re-indexed and renamed $Q_i$ as follows, $$\{Q'_{0,0}, Q'_{1,0}, \text{ReQ}'_{1,1}, \text{ImQ}'_{1,1}, Q'_{2,0}, \text{ReQ}'_{2,1}, \text{ImQ}'_{2,1}, \text{ReQ}'_{2,2}, \ldots\} \leftrightarrow \{Q_1, Q_2, Q_3, Q_4, Q_5, Q_6, Q_7, Q_8, \ldots\}. \quad (54)$$

and similar transformations are used to create $\alpha_i$, $\beta_{ij}$, and $\gamma_i$. Eq. (51) can then be written as $$\Delta G_{\text{var}} = \sum_{i=1}^{\infty} \alpha_i Q_i + \sum_{i=1}^{\infty}\sum_{j=1}^{\infty} \beta_{ij} Q_i Q_j - \sum_{i=1}^{\infty} \gamma_i Q_i^2 \quad (55)$$

$$= \sum_{i=1}^{\infty} \alpha_i Q_i + \sum_{i=1}^{\infty}\sum_{j=1}^{\infty} (\beta_{ij} - \delta_{ij}\gamma_i) Q_i Q_j \quad (56)$$

or in matrix notation, $$\Delta G_{\text{var}} = \vec{Q}^T \vec{B} \vec{Q} + \vec{Q}^T \vec{A} \quad (57)$$

$$= \left(\vec{Q} + \frac{1}{2}\vec{B}^{-1}\vec{A}\right)^T \vec{B} \left(\vec{Q} + \frac{1}{2}\vec{B}^{-1}\vec{A}\right) - \frac{1}{4}\vec{A}^T \vec{B}^{-1} \vec{A} \quad (58)$$

where $\vec{Q}$ is the vector formed by the $Q_i$, $\vec{A}$ is the vector formed by the $\alpha_i$, $\vec{B}$ is the symmetric matrix formed by the $(\beta_{ij} - \delta_{ij}\gamma_i)$, and completion of the square has been used to arrive at Eq. (58). Since $\vec{Q}^T \vec{B} \vec{Q}$ in Eq. (57) corresponds to the ligand desolvation penalty, which must be greater than zero for chemically reasonable geometries, the matrix $\vec{B}$ is positive definite and the extremum of $\Delta G_{\text{var}}$ is a minimum.[5] From Eq. (58) the optimum values of the multipoles, $\vec{Q}^{opt}$ and the minimum variational binding energy, $\Delta G_{\text{var}}^{opt}$ are obtained, $$\vec{Q}^{opt} = -\frac{1}{2}\vec{B}^{-1}\vec{A} \quad (59)$$

$$\Delta G_{\text{var}}^{opt} = -\frac{1}{4}\vec{A}^T \vec{B}^{-1} \vec{A}. \quad (60)$$

$\Delta G_{\text{var}}^{opt}$ is always negative because $\vec{B}^{-1}$ is also positive definite.

To solve for the optimal multipole distribution with the monopole (total charge) fixed ($Q_1 = \mathcal{Q}$), the equation for the remaining optimal multipoles ($i \neq 1$) is, $$2\sum_{j \neq 1} (\beta_{ij} - \delta_{ij}\gamma_i) Q_j^{opt} + (2\beta_{i1}\mathcal{Q} + \alpha_i) = 0 \quad (61)$$

which is analogous to Eq. (59).

The above matrix equations, with the dimension truncated at $i_{max} = (l_{max}+1)^2$, can be solved numerically by relatively modest computational resources. In practice, since the $\alpha_i$ and $\beta_{ij}$ contain a summation over an infinite number of terms, a second cutoff value of $l_{cut}$ must be used to truncate the innermost sum in Eqs. (25) and (46). When $l_{max}$ and $l_{cut}$ are sufficiently large, $\Delta G_{\text{var}}^{opt}$ converges and the incremental advantage of including more multipoles essentially vanishes.

For any given receptor and geometry, we have thus described a method to determine the charge distribution of the tightest binding ligand as a set of multipoles. The deviation of the binding free energy from the optimum for any test ligand can be calculated by subtracting Eq. (60) from Eq. (58) and using Eq. (59) to eliminate $\vec{A}$,

TABLE I

| | $C(l', 1, l; m - m', m')$,[a] | | |
|---|---|---|---|
| | $m' = 1$ | $m' = 0$ | $m' = -1$ |
| $l = l' + 1$ | $\left[\dfrac{(l'+m)(l'+m+1)}{(2l'+1)(2l'+2)}\right]^{1/2}$ | $\left[\dfrac{(l'-m+1)(l'+m+1)}{(2l'+1)(l'+1)}\right]^{1/2}$ | $\left[\dfrac{(l'-m)(l'-m+1)}{(2l'+1)(2l'+2)}\right]^{1/2}$ |
| $l = l'$ | $-\left[\dfrac{(l'+m)(l'-m+1)}{2l'(l'+1)}\right]^{1/2}$ | $\dfrac{m}{[l'(l'+1)]^{1/2}}$ | $\left[\dfrac{(l'-m)(l'+m+1)}{2l'(l'+1)}\right]^{1/2}$ |
| $l = l' - 1$ | $\left[\dfrac{(l'-m)(l'-m+1)}{2l'(2l'+1)}\right]^{1/2}$ | $-\left[\dfrac{(l'-m)(l'+m)}{l'(2l'+1)}\right]^{1/2}$ | $\left[\dfrac{(l'+m+1)(l'+m)}{2l'(2l'+1)}\right]^{1/2}$ |

[a]from reference 4

APPENDIX REFERENCES

[1] J. D. Jackson, *Classical Electrodynamics*, 2nd ed. (John Wiley and Sons, New York, 1975).

[2] L. Greengard, *The Rapid Evaluation of Potential Fields in Particle Systems* (MIT Press, Cambridge, Mass., 1988).

[3] M. E. Rose, J. Math. & Phys. 37, 215 (1958);

[4] M. E. Rose, *Elementary Theory of Angular Momentum* (John Wiley and Sons, New York, 1957).

[5] G. Strang, *Introduction to Applied Mathematics* (Wellesley-Cambridge Press, Wellesley, Mass., 1986).

Having now described a few embodiments of the present computer-implemented process, it should be apparent to those skilled in the art that the foregoing is merely illustrative and not limiting, having been presented by way of example only. Numerous modifications and other embodiments are within the scope of one of ordinary skill in the art and are contemplated as falling within the scope of the present process as defined by the appended claims and equivalent thereto.

What is claimed is:

1. A computer-implemented process for identifying properties of a ligand for binding to a target molecule in a solvent comprising the steps of:

receiving an indication of a selected shape of the ligand, defined in three dimensions, which complements a shape of a selected portion of the target molecule, defined in three dimensions;

determining a representation of a charge distribution which minimizes electrostatic contribution to binding free energy between the ligand and the target molecule in the solvent.

2. The computer-implemented process of claim 1, wherein the representation of the charge distribution is a set of multipoles.

3. The computer-implemented process of claim 1, further comprising the step of identifying a ligand having point charges that match the representation of the charge distribution.

4. The computer-implemented process of claim 2, further comprising the step of identifying a ligand having point charges that match the representation of the charge distribution.

5. The computer-implemented process of claim 1, further comprising the step of designing a combinatorial library containing ligands having point charges that match the representation of the charge distribution.

6. The computer-implemented process of claim 2, further comprising the step of designing a combinatorial library containing ligands having point charges that match the representation of the charge distribution.

* * * * *

UNITED STATES PATENT AND TRADEMARK OFFICE
CERTIFICATE OF CORRECTION

PATENT NO.         : 6,230,102 B1
APPLICATION NO.    : 09/055475
DATED              : May 8, 2001
INVENTOR(S)        : Tidor et al.

Page 1 of 1

It is certified that error appears in the above-identified patent and that said Letters Patent is hereby corrected as shown below:

Please insert the following in the specification of U.S. Patent No. 6,230,102 at column 1, line 7:

-- Sponsorship Information
This invention was made with government support under Grant Numbers P01 GM056552, R01 GM055758, P01 GM066524, and R01 CA096504 awarded by the National Institutes of Health and under Grant Number MCB-0091001 awarded by the National Science Foundation. The government has certain rights in the invention. --

Signed and Sealed this
Thirteenth Day of March, 2012

David J. Kappos
*Director of the United States Patent and Trademark Office*